(12) United States Patent
Thakor et al.

(10) Patent No.: US 12,089,823 B2
(45) Date of Patent: Sep. 17, 2024

(54) DEVICES, SYSTEMS, AND METHODS FOR SELF-COLLECTION OF BIOLOGICAL SAMPLES

(71) Applicant: Teal Health, Inc., Menlo Park, CA (US)

(72) Inventors: Avnesh Thakor, Menlo Park, CA (US); Kara Egan, Menlo Park, CA (US)

(73) Assignee: Teal Health, Inc., San Francisco, CA (US)

( * ) Notice: Subject to any disclaimer, the term of this patent is extended or adjusted under 35 U.S.C. 154(b) by 0 days.

(21) Appl. No.: 17/839,377

(22) Filed: Jun. 13, 2022

(65) Prior Publication Data

US 2022/0395259 A1 Dec. 15, 2022

Related U.S. Application Data

(60) Provisional application No. 63/210,492, filed on Jun. 14, 2021.

(51) Int. Cl.
  *A61B 10/00* (2006.01)
  *A61B 10/02* (2006.01)

(52) U.S. Cl.
  CPC .. *A61B 10/0045* (2013.01); *A61B 2010/0006* (2013.01); *A61B 2010/0074* (2013.01); *A61B 2010/0208* (2013.01); *A61B 2010/0216* (2013.01)

(58) Field of Classification Search
  None
  See application file for complete search history.

(56) References Cited

U.S. PATENT DOCUMENTS

| | | | |
|---|---|---|---|
| 3,776,219 A | * | 12/1973 | Brown ............... A61B 10/0291 600/572 |
| 3,815,580 A | | 6/1974 | Oster |
| 4,318,414 A | | 3/1982 | Schuster et al. |
| 4,662,381 A | | 5/1987 | Inaba |
| 4,700,903 A | | 10/1987 | Henn |

(Continued)

FOREIGN PATENT DOCUMENTS

| CN | 201023099 Y | 2/2008 |
|---|---|---|
| CN | 104622518 A | 5/2015 |

(Continued)

OTHER PUBLICATIONS

English machine translation for SE-464499-B, patents.google.com, 4 pages, printed on Sep. 12, 2022 (Year: 2022).*

(Continued)

*Primary Examiner* — Matthew Kremer
(74) *Attorney, Agent, or Firm* — COOLEY LLP

(57) ABSTRACT

A universal single-handed device for self-collection of a biological sample is described herein. The single-handed device may comprise a sheath comprising a distal end for insertion into a portion of a user's body, a shaft at least partially within the sheath, having a collection head for collecting the biological sample positioned at the distal end thereof, and an actuator coupled to the shaft to transition the distal end between an open configuration and a closed configuration. The collection head is covered by the distal end in the closed configuration and is exposed when the distal end is in the open configuration.

20 Claims, 15 Drawing Sheets

(56) References Cited

U.S. PATENT DOCUMENTS

| | | |
|---|---|---|
| D331,625 S | 12/1992 | Price et al. |
| 5,191,899 A | 3/1993 | Strickland et al. |
| D336,957 S | 6/1993 | Koros et al. |
| D344,903 S | 3/1994 | Gampp, Jr. et al. |
| D351,227 S | 10/1994 | Patton et al. |
| 5,445,164 A | 8/1995 | Worthen et al. |
| D369,408 S | 4/1996 | Laun |
| D372,311 S | 7/1996 | Koros et al. |
| 5,543,115 A | 8/1996 | Karakawa |
| D373,634 S | 9/1996 | Brown |
| D381,418 S | 7/1997 | Erskine et al. |
| D381,426 S | 7/1997 | Koros et al. |
| D382,342 S | 8/1997 | Rosen |
| 5,787,891 A | 8/1998 | Sak |
| 5,827,305 A * | 10/1998 | Gordon ............... A61B 10/0266 606/159 |
| D407,488 S | 3/1999 | Injev |
| D413,382 S | 8/1999 | Maissami |
| D441,447 S | 5/2001 | Hjertman et al. |
| D443,058 S | 5/2001 | Mulhauser et al. |
| D443,930 S | 6/2001 | Nestenborg |
| 6,346,086 B1 * | 2/2002 | Maksem ............ A61B 10/0291 600/572 |
| D466,214 S | 11/2002 | Otsuka |
| D538,936 S | 3/2007 | Böhmel et al. |
| D553,738 S | 10/2007 | Simonson |
| D581,534 S | 11/2008 | Dong et al. |
| D585,989 S | 2/2009 | Leroy |
| D588,888 S | 3/2009 | Yung-Kuan |
| D589,618 S | 3/2009 | Hasebe |
| D590,056 S | 4/2009 | McCrary et al. |
| D593,202 S | 5/2009 | Petersen |
| D601,252 S | 9/2009 | Ra |
| D603,502 S | 11/2009 | Petersen |
| D612,052 S | 3/2010 | McCollam et al. |
| D615,196 S | 5/2010 | Doll |
| D619,707 S | 7/2010 | East |
| 8,152,739 B1 | 4/2012 | McCully |
| D663,836 S | 7/2012 | Ruiz, Sr. et al. |
| D669,981 S | 10/2012 | Ruiz, Sr. et al. |
| 8,287,466 B2 | 10/2012 | Weikel, Jr. et al. |
| 8,460,209 B2 | 6/2013 | Klein |
| D692,998 S | 11/2013 | Broberg et al. |
| 8,672,860 B2 | 3/2014 | Moore et al. |
| 8,672,861 B2 | 3/2014 | Klein |
| D704,336 S | 5/2014 | Chon et al. |
| D708,323 S | 7/2014 | Reyes et al. |
| 8,801,628 B2 | 8/2014 | Teschendorf |
| D720,070 S | 12/2014 | Khalaj |
| 8,961,896 B2 | 2/2015 | McSherry |
| D747,477 S | 1/2016 | Freigang et al. |
| D749,725 S | 2/2016 | Sauer |
| D750,270 S | 2/2016 | Ching et al. |
| 9,282,950 B2 | 3/2016 | Klein |
| 9,451,935 B2 | 9/2016 | McSherry |
| D779,059 S | 2/2017 | Nino et al. |
| D798,446 S | 9/2017 | Nino et al. |
| D809,138 S | 1/2018 | Khan et al. |
| D810,273 S | 2/2018 | Maier et al. |
| D831,210 S | 10/2018 | Nelson et al. |
| D832,426 S | 10/2018 | Holton et al. |
| D835,273 S | 12/2018 | Orr et al. |
| D859,652 S | 9/2019 | Teufel |
| 10,456,118 B2 | 10/2019 | McSherry |
| D866,757 S | 11/2019 | Diluzio et al. |
| D873,433 S | 1/2020 | Hagiwara |
| D875,926 S | 2/2020 | Lee et al. |
| D883,475 S | 5/2020 | Boyaval et al. |
| D921,196 S | 6/2021 | Wang |
| D938,583 S | 12/2021 | Yan et al. |
| D950,723 S | 5/2022 | Leibowitz |
| D958,398 S | 7/2022 | O'Leary |
| D975,847 S | 1/2023 | Goh et al. |
| D983,368 S | 4/2023 | Leibowitz |
| D983,970 S | 4/2023 | Vaughan et al. |
| D1,006,991 S | 12/2023 | Vaughan et al. |
| D1,021,130 S | 4/2024 | Thakor et al. |
| 2001/0039058 A1 | 11/2001 | Iheme et al. |
| 2002/0068881 A1 | 6/2002 | Kobren et al. |
| 2002/0087096 A1 * | 7/2002 | Anderson .......... A61B 10/0045 600/572 |
| 2002/0106809 A1 | 8/2002 | Cesarczyk |
| 2004/0214200 A1 | 10/2004 | Brown et al. |
| 2004/0245125 A1 | 12/2004 | Trkulja |
| 2006/0074407 A1 | 4/2006 | Padget et al. |
| 2008/0166818 A1 | 7/2008 | Ennis |
| 2008/0188769 A1 * | 8/2008 | Lu ......................... A61B 10/02 600/569 |
| 2008/0194912 A1 * | 8/2008 | Trovato ................. A61B 34/72 600/118 |
| 2009/0082695 A1 | 3/2009 | Whitehead |
| 2009/0275859 A1 | 11/2009 | Kim |
| 2010/0160816 A1 | 6/2010 | Parihar et al. |
| 2012/0157878 A1 | 6/2012 | Mendez |
| 2012/0282616 A1 | 11/2012 | Zeijlstra |
| 2013/0066233 A1 * | 3/2013 | Klein .................. A61B 10/0291 600/572 |
| 2013/0253372 A1 | 9/2013 | Klein |
| 2013/0338533 A1 | 12/2013 | Olsen |
| 2014/0051178 A1 | 2/2014 | Niggel et al. |
| 2014/0128732 A1 | 5/2014 | Roy et al. |
| 2014/0221987 A1 | 8/2014 | Jeong et al. |
| 2015/0088032 A1 | 3/2015 | Lee-Sepsick |
| 2015/0088151 A1 | 3/2015 | Hatta |
| 2015/0297196 A1 * | 10/2015 | Ching ................ A61B 10/0045 600/572 |
| 2016/0242901 A1 | 8/2016 | Keren |
| 2017/0042518 A1 | 2/2017 | Sak et al. |
| 2017/0303903 A1 | 10/2017 | De et al. |
| 2018/0021771 A1 | 1/2018 | Tamir |
| 2018/0052096 A1 | 2/2018 | Wan et al. |
| 2018/0078242 A1 | 3/2018 | Aghdam |
| 2018/0141043 A1 | 5/2018 | Malcolmson et al. |
| 2020/0116598 A1 | 4/2020 | Ling |
| 2021/0137506 A1 | 5/2021 | Thakor |
| 2022/0257093 A1 | 8/2022 | Tarke et al. |
| 2023/0129323 A1 | 4/2023 | Bailey et al. |
| 2023/0143077 A1 | 5/2023 | Higgins et al. |
| 2023/0172591 A1 | 6/2023 | Robbins et al. |

FOREIGN PATENT DOCUMENTS

| | | | |
|---|---|---|---|
| EP | 3338644 A1 | 6/2018 | |
| EP | 3338664 A2 | 6/2018 | |
| SE | 464499 B * | 5/1991 | ......... A61B 10/0291 |
| WO | WO-0053099 A1 | 9/2000 | |
| WO | WO-2007045896 A1 | 4/2007 | |
| WO | WO-2010085841 A1 | 8/2010 | |
| WO | WO-2016160454 A1 | 10/2016 | |
| WO | WO-2018091906 A1 | 5/2018 | |
| WO | WO-2019172828 A1 * | 9/2019 | |
| WO | WO-2020028143 A | 2/2020 | |
| WO | WO-2021231180 A1 | 11/2021 | |
| WO | WO-2022266008 A1 | 12/2022 | |

OTHER PUBLICATIONS

United States Patent and Trademark Office, International Search Report and Written Opinion for PCT/US2019/043440, Oct. 22, 2019, 16 pages.

European Patent Office, Extended European Search Report for EP 3829451, Mar. 22, 2022, 9 pages.

United States Patent and Trademark Office, International Search Report for PCT/US2019/043440, Oct. 22, 2019, 3 pages.

[Author Unknown] Papcone® (Cervical Cell Scraper), 501(k) No. K083012 Summary/Notification, Otto Bock PUR Life Science GmbH, Germany, Date Prepared: Feb. 4, 2009, 5 pages.

Enechukwu, C. I. et al. "Comparative study on the adequacy of cervical smears using wooden Ayre's spatula, VS Papcone® sampling device." Gynecologic Oncology Reports (2021); 38: 100860. 4 pages.

(56) References Cited

OTHER PUBLICATIONS

International Preliminary Report on Patentability for International Application No. PCT/US2019/043440, dated Feb. 2, 2021, 14 pages.
International Search Report and Written Opinion for International Application No. PCT/US2022/033294, mailed Oct. 25, 2022, 22 pages.
Lukic, A. et al. "Satisfactory sampling in cytological cervical diagnosis: comparison between a conventional and a new sampling device." Anticancer Research (2013); 33(3): 917-922.
International Preliminary Report on Patentability for International Application No. PCT/US2022/033294, mailed Dec. 28, 2023, 14 pages.

\* cited by examiner

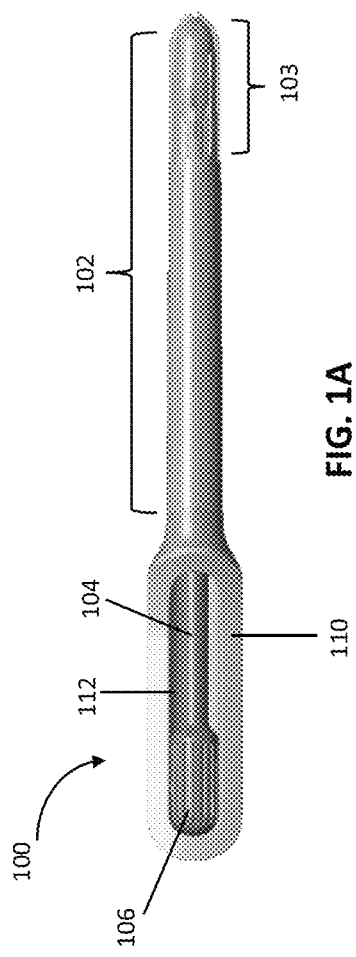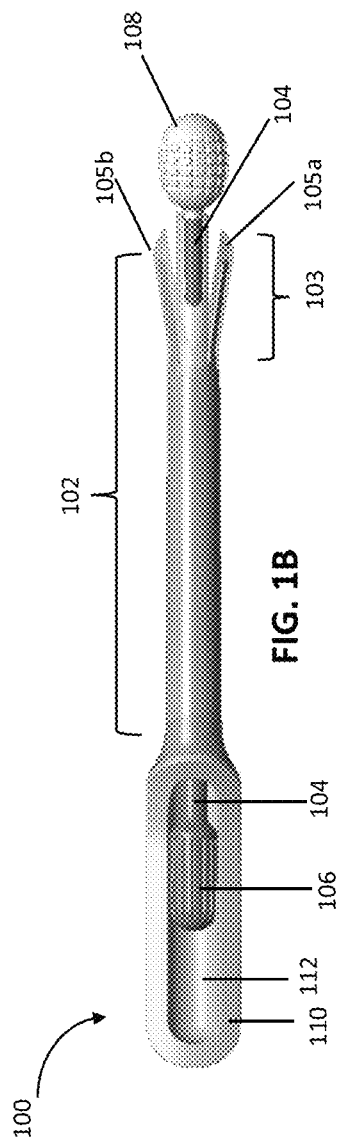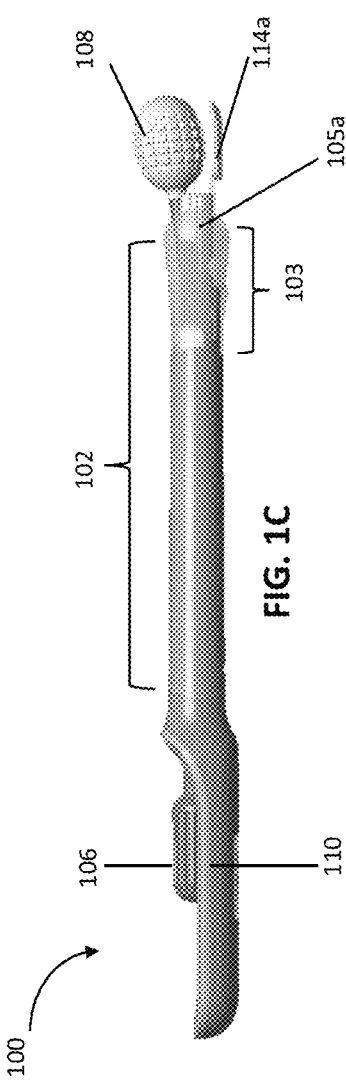

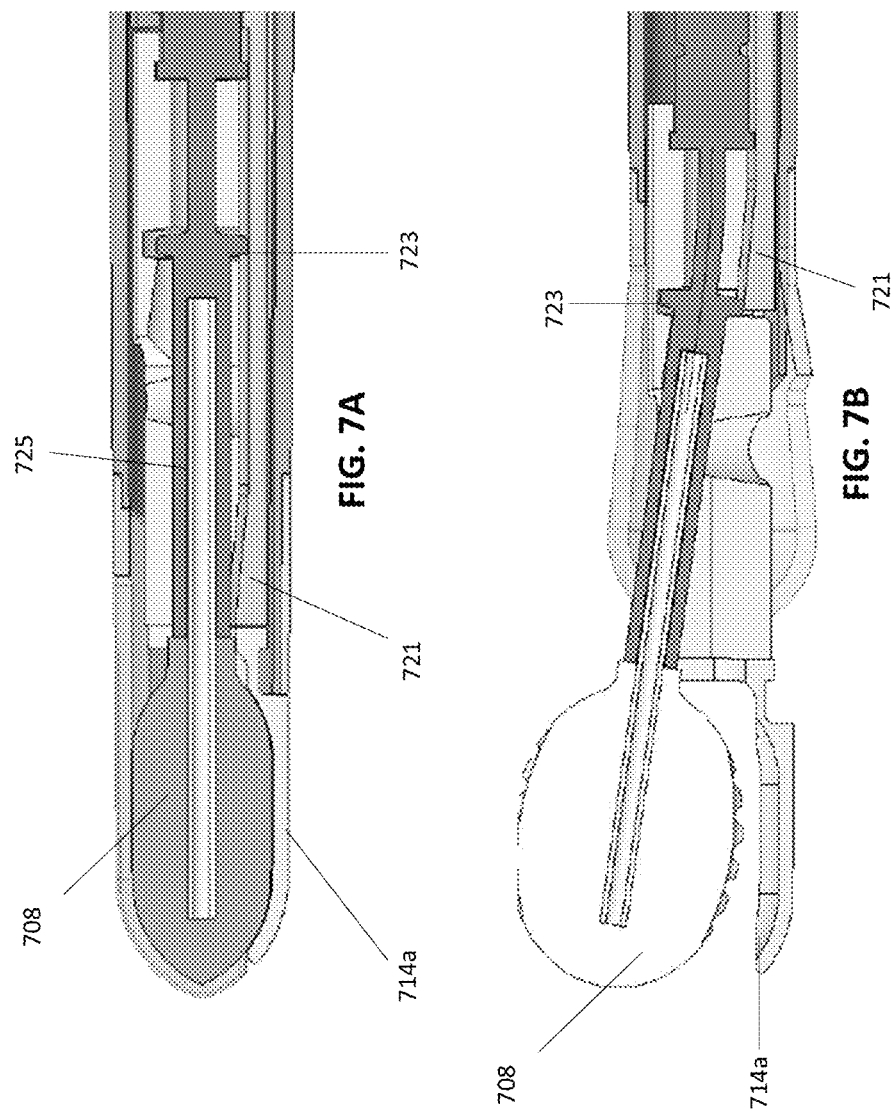

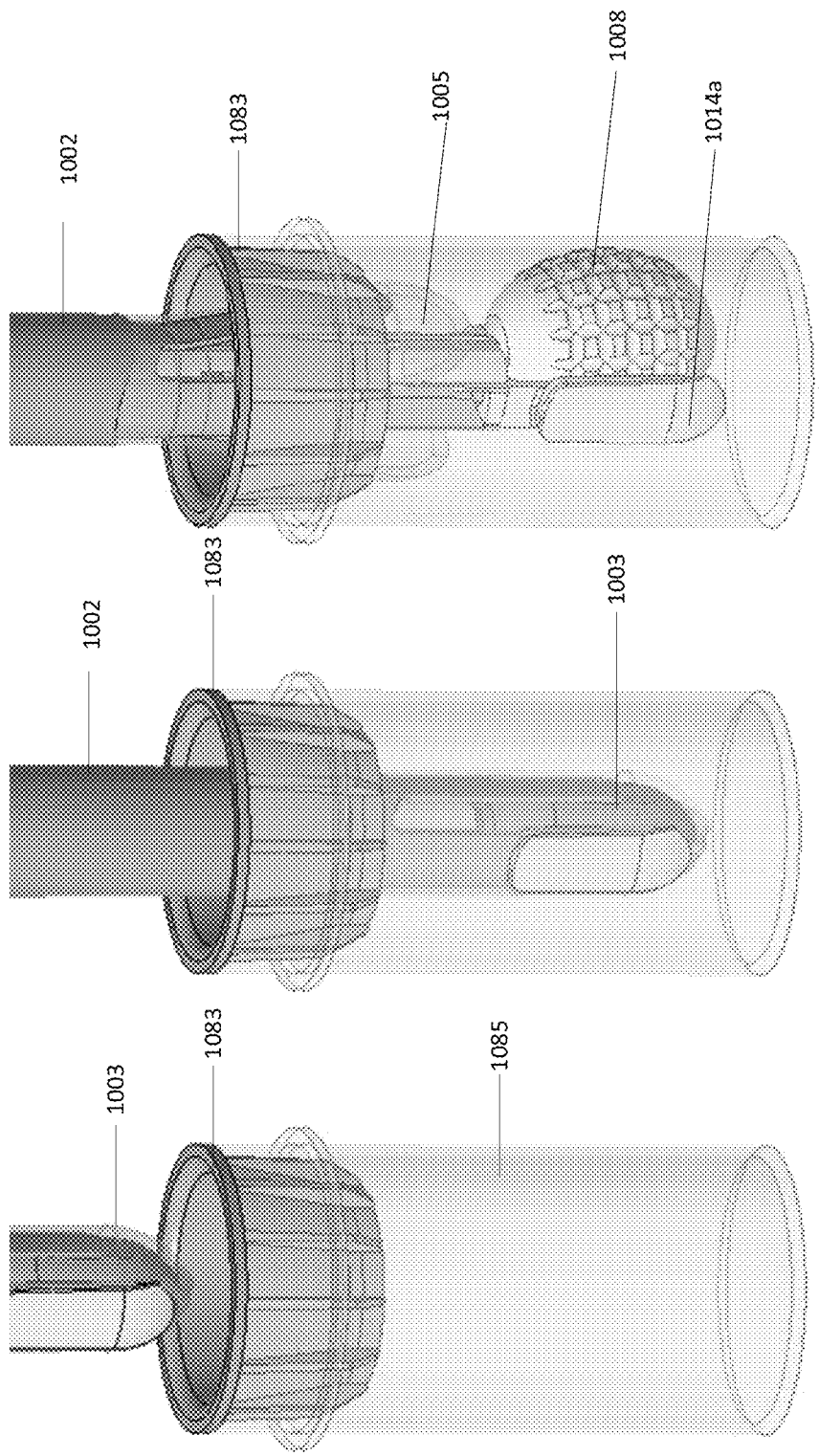

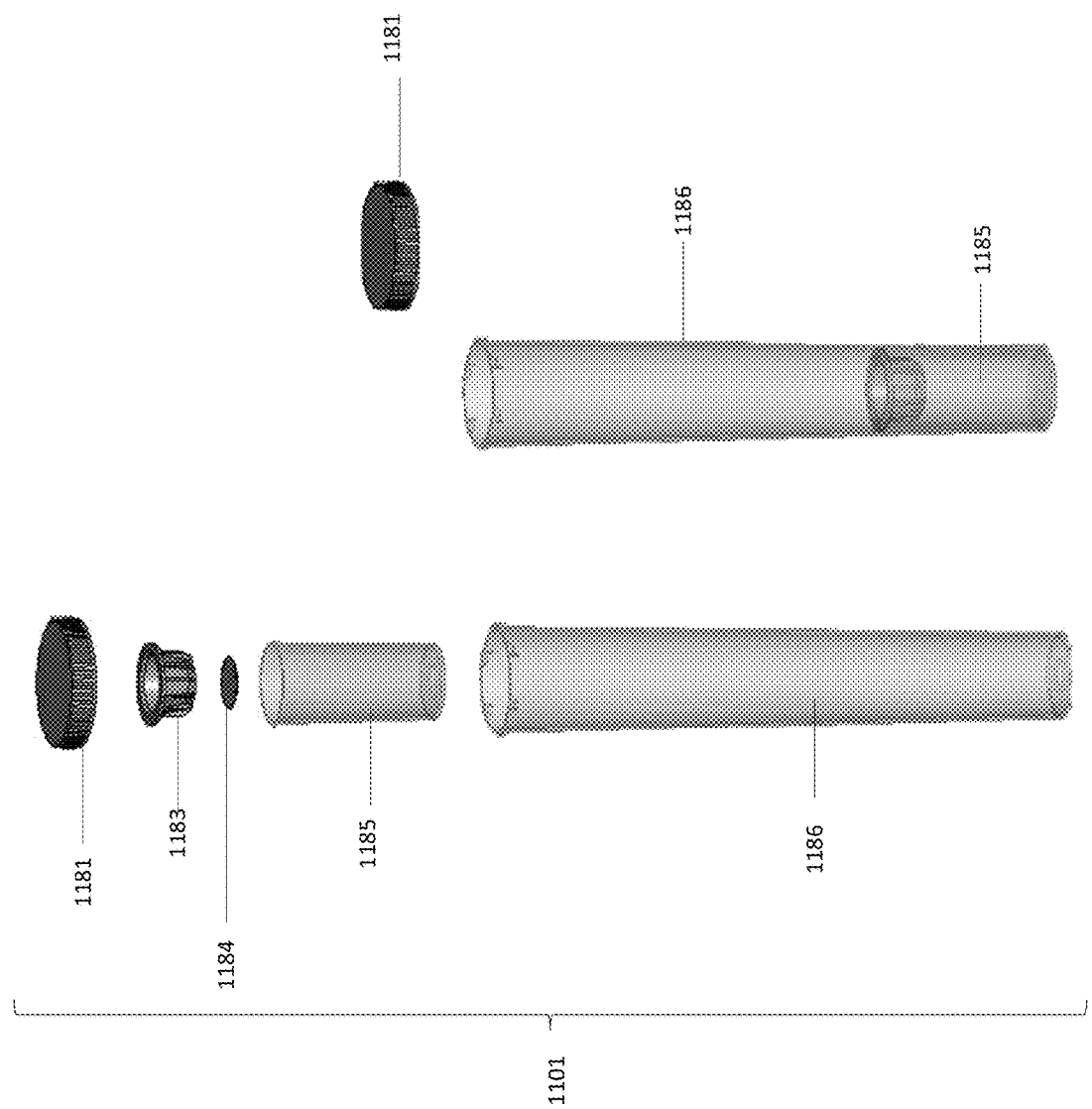

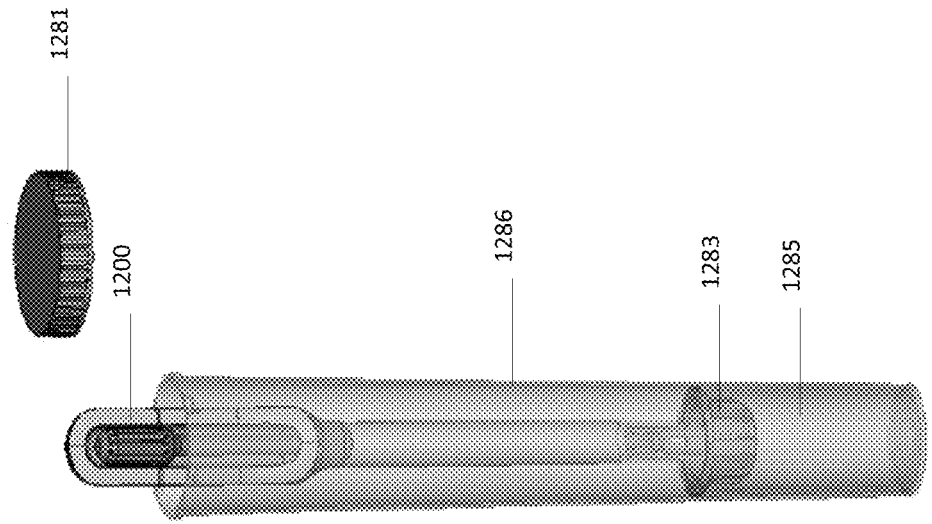
FIG. 12B
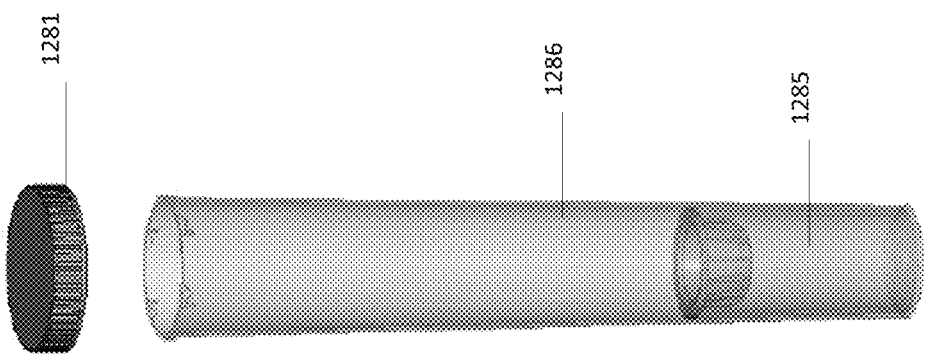
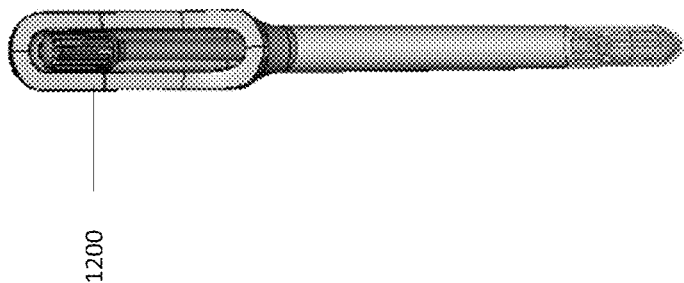
FIG. 12A

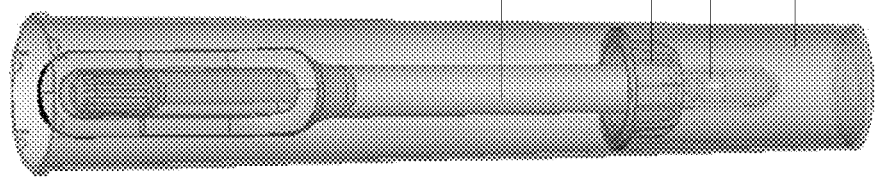
FIG. 12D
FIG. 12C

DEVICES, SYSTEMS, AND METHODS FOR SELF-COLLECTION OF BIOLOGICAL SAMPLES

CROSS-REFERENCE TO RELATED APPLICATIONS

This application claims priority to U.S. Patent Application Ser. No. 63/210,492 filed Jun. 14, 2021, which is hereby incorporated in its entirety by this reference.

TECHNICAL FIELD

This invention relates generally to the field of self-collection of biological samples.

BACKGROUND

Screening for ailments such as sexually transmitted diseases, infections (e.g., infections during pregnancy, etc.), other diseases (e.g., autoimmune diseases, endometriosis, uterine fibroids, polycystic kidneys, etc.), cancers (e.g., breast cancer, cervical cancer, colon cancer, etc.) and/or other general health conditions (e.g., hormone levels, folate levels, semen exposure levels, toxin levels, etc.) may involve collecting biological samples from a subject and then analyzing the biological samples. To collect biological samples, one or more devices may be inserted into an opening and/or lumen of a subject's body. Biological samples may be collected from the opening and/or lumen and later analyzed. Traditionally, biological samples are collected in a medical facility, processed, and then transported to a laboratory for analysis. Collecting biological samples in a medical facility may be time consuming. For example, collecting biological samples may involve wait time at the medical facility, travel time to the medical facility, etc. Additionally, some procedures for collecting biological samples may be invasive and painful. Furthermore, subjects may have to endure embarrassment and physical discomfort of having medical professionals view and access portions of their body to collect the biological samples.

More recently, some advances have been made towards developing devices that may be inserted into a cavity and/or lumen of a subject's body for self-collection of biological samples. Existing devices, however, are challenging to use. For instance, some existing devices have bulky designs making them intimidating and uncomfortable for subjects to insert them into their body. These existing devices are not ergonomic. Most existing devices are not designed to optimize the collection of biological samples. For instance, these devices do not have designs to engage with the biological samples and adhere to the biological samples to maximize the collection of biological samples. Furthermore, these existing devices are not designed to be sensitive to the tissues and/or cells surrounding the portion of the body from which the biological sample may be collected. Additionally, most existing devices are not designed to prevent loss of biological samples after the samples have been collected and before the samples have been analyzed.

Therefore, additional devices, systems, and methods are needed for self-collection of biological samples so that a subject may ergonomically be able to maximize collection of biological samples in their private setting without assistance from others.

SUMMARY

Described herein are variations of kit, devices, and methods for self-collection of a biological sample. In some variations, a universal single-handed device may comprise a sheath comprising a distal end for insertion into a portion of a user's body, a shaft at least partially within the sheath, having a collection head for collecting the biological sample positioned at the distal end thereof, and an actuator coupled to the shaft to transition the distal end between an open configuration and a closed configuration. The collection head may be covered by the distal end in the closed configuration and may be exposed when the distal end is in the open configuration.

In some variations, the actuator may be at least one of a knob, a roller, button, or a slider. In some variations, the single-handed device may further comprise a slider coupled to the shaft. The slider may comprise a distal extension to hold the collection head. In the open configuration, the collection head may be configured to laterally deflect from the distal extension of the slider.

In some variations, the distal end may comprise at least two flexible segments along a longitudinal axis of the single-handed device. The at least two flexible segments may be configured to part from each other in the open configuration, thereby creating an opening in the distal end to expose the collection head. In some variations, the device may further comprise three flexible segments.

In some variations, the device may further comprise a handle attached to a proximal end of the sheath. The actuator may be disposed within the handle. In some variations, the actuator may include a feedback mechanism to indicate a movement of the collection head. The feedback mechanism may be configured to indicate one of an amount of displacement of the collection head or an amount of rotation of the collection head. In some variations, the feedback mechanism may comprise at least one of an audible feedback, a visual feedback, or a haptic feedback.

In some variations, the collection head may comprise polyurethane. In some variations, at least a portion of the collection head may comprise a honeycomb pattern or an open cell lattice. The honeycomb pattern or the open lattice pattern may engage with a cervical os of a user, thereby enabling collection of the biological sample. The biological sample may be cervical cells.

In some variations, the collection head may comprise at least one of a brush, a sponge, a protrusion, or a bristle. In some variations, the distal end may comprise a biocompatible material. The distal end may comprise lubricous material. In some variations, the collection head may include a marker configured to react with the biological sample, thereby producing a visual change in the collection head. In some variations, a density of the collection head may be between 20 ppi and 90 ppi.

In some variations, a kit for self-collecting and storing a biological sample may comprise a universal single-handed device configured to be self-inserted into a portion of a user's body. The universal single-handed device may include a sheath comprising a distal end configured to transition between an open configuration and a closed configuration, and a collection head configured to collect the biological sample. In the closed configuration, the distal end may be configured to cover the collection head. In the open configuration, the collection head may be configured to advance distally and the distal end may be configured to expose the collection head. The kit may also comprise a vial to store the biological sample.

In some variations, the kit may further comprise a frame including a first cavity to receive the universal single-handed device and a second cavity to receive the vial. While transferring the biological sample from the universal single-handed device to the vial, the frame may be configured to hold the vial in an upright position.

In some variations, the vial may include an hourglass shape to guide at least a portion of the sheath into the vial. After collecting the biological sample, the collection head may be configured to expand. In some variations, a diameter of a bottom portion of the vial may be greater than a diameter of the collection head when it is expanded. In some variations, the vial may include a preservative fluid to store the biological sample. The vial may include at least one reagent to analyze the biological sample. In some variations, the collection head may include polyurethane.

In some variations, a method for self-collecting a biological sample may comprise inserting a distal end of a single-handed device into a lumen of a user's body. The single-handed device may comprise a sheath including a distal end, a shaft at least partially within the sheath, a collection head positioned at a distal end of the shaft, and an actuator coupled to the shaft to transition the distal end between an open configuration and a closed configuration. The collection head may be covered by the distal end in the closed configuration. The method may also include actuating the actuator to transition the distal end to the open configuration, thereby causing the collection head to advance distally, rotating the collection head to collect the biological sample, actuating the actuator to transition the distal end to the closed configuration, thereby retracting the collection head proximally such that the collection head is covered by the distal end, and withdrawing the single-handed device.

In some variations, the single-handed device may further comprise a handle coupled to a proximal end of the sheath, and actuating the actuator may comprise advancing or retracting the actuator within a slot of the handle. In some variations, the lumen of the user's body may be a vaginal canal, and actuating the actuator may transition the distal end to the open configuration, and the distal end may appose a vaginal wall of the user. The distal end may include at least two flexible segments and actuating the actuator may transition the distal end to the open configuration and may align via the at least two flexible segments, the collection head with the user's cervix. In some variations, the method may further comprise displacing, via the at least two flexible segments, tissues surrounding the user's cervix.

In some variations, the biological sample may at least be one of cervicovaginal fluid, menstrual blood, interstitial fluid, cervical secretion, semen, fetal tissue, trophoblast cell, placental tissue, reproductive cell, or endometrial cell.

BRIEF DESCRIPTION OF THE DRAWINGS

FIG. 1A depicts an exemplary variation of a top view of a universal single-handed device for self-collection of a biological sample when the distal end is in a closed configuration.

FIG. 1B depicts an exemplary variation of a top view of a universal single-handed device for self-collection of a biological sample when the distal end is in an open configuration.

FIG. 1C depicts an exemplary variation of a side view of a universal single-handed device for self-collection of a biological sample.

FIG. 7A depicts an exemplary variation of a collection head of a universal single-handed device for self-collection of a biological sample when the collection head is in a compressed state.

FIG. 7B depicts an exemplary variation of a collection head of a universal single-handed device for self-collection of a biological sample when the collection head is in an expanded state.

FIGS. 10A-10C illustrate an exemplary variation of collecting a biological sample in a vial using a universal single-handed device.

FIG. 11A depicts an exploded view of an exemplary variation of a vial.

FIG. 11B depicts an exemplary variation of a vial.

FIGS. 12A-12E illustrate an exemplary variation of collecting a biological sample in a vial using a universal single-handed device described herein.

DETAILED DESCRIPTION

Figure 1D:
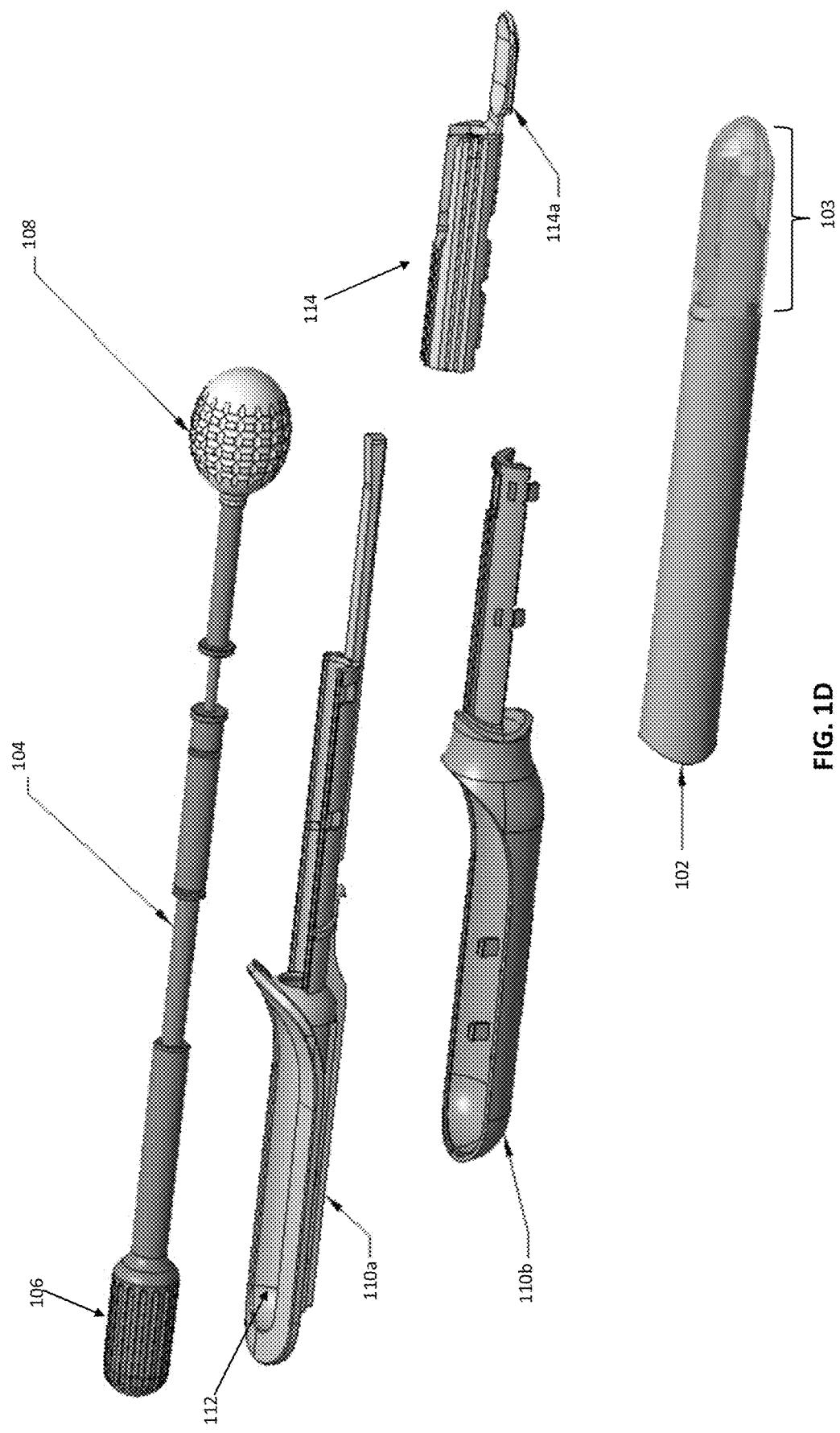
FIG. 1D depicts an exemplary variation of an exploded view of a universal single-handed device for self-collection of a biological sample.

Non-limiting examples of various aspects and variations of the invention are described herein and illustrated in the accompanying drawings.

Described herein are devices, systems, and methods for self-collection of biological samples. At least a portion of the devices described herein may be configured to be inserted into a portion of a user's body to collect the biological samples. The devices described herein may be designed to be ergonomic. For example, the devices described herein may be designed such that a user may use a single hand (e.g., either the left hand or right hand, or even both hands if desired) to self-collect the biological samples. Additionally, the devices described herein may be designed to prevent trauma during insertion. Furthermore, the devices described herein may include one or more mechanisms to align, position, and/or orient parts of these devices to help maximize engagement with the tissue interface from which a biological sample is to be collected and also help maximize retention of the biological sample during self-collection. The devices described herein may also be configured to prevent loss of the biological sample after the biological sample has been collected from a portion of the user's body. The devices described herein may also include a feedback mechanism to help the user collect the biological sample, for example, by indicating a type or amount of movement required to collect the biological sample.

Biological samples to be self-collected may include any suitable biological sample that may be collected from the user's body. For example, biological samples may include bodily tissues (e.g., various cells, etc.), bodily fluids (blood, secretions, etc.), or a combination thereof, and/or the like. In some variations, biological samples may include cervical cells, cervicovaginal fluid, menstrual blood, interstitial fluid, cervical secretions, semen, fetal tissue, trophoblast cells, placental tissue, reproductive cells, endometrial cells, and/or the like. In some variations, at least a portion of the devices described herein may be configured to be inserted into a lumen or opening of a user's body to collect biological samples from the lumen or opening and/or parts surrounding the lumen. For example, the lumen or opening may include the vaginal canal, anus, bowel and enteric tract, biliary ducts, oropharyngeal space/throat, ear, nasal, trachea or bronchus and/or the like.

Devices

Generally, the self-collection devices described herein may be universal single-handed devices for self-collection of biological samples. The devices may comprise a sheath having a distal end for insertion into a portion of a user's body. The devices may also comprise a shaft that may be partially within the sheath (e.g., disposed within the sheath, positioned within the sheath, and/or the like). An actuator may be coupled to the shaft to transition the distal end of the sheath between an open configuration and a closed configuration. The shaft may have a collection head at the distal end for the collection of a biological sample.

In the closed configuration, the collection head may be covered by the distal end of the sheath. In this way, the collection head is protected against contamination or damage prior to and during insertion into the lumen or opening. In the open configuration, the collection head may be exposed, thus allowing for self-collection once the collection head has been appropriately placed at or adjacent the site of collection/target tissue interface. In some variations, the distal end of the sheath comprises flexible segments that are integral with the sheath and are configured to part or separate in the open configuration. Any number of flexible segments may be used, e.g., two, three, four, etc. In variations in which the sheath has flexible distal segments, the sheath may be actuated to separate or part the flexible distal segments thus creating an opening in the distal end of the sheath while also providing mechanical displacement of surrounding tissues to allow unhindered access of the collection head to the target tissue interface. In the open configuration, the collection head is exposed so that it may be allowed to advance and retract in an unhindered manner from and into the sheath to collect a biological sample.

The device(s) may comprise an actuator that is coupled to a shaft to help transition the sheath from the open to the closed configuration. Any suitable actuator may be used, for example, the actuator may be a button, a roller, a knob, a pull, a slide, a switch, combinations thereof, and the like. In some variations, the actuator comprises a slider that is coupled to the shaft. The slider may comprise an extension at its distal end configured to house, hold, support, or stabilize the collection head. In the open configuration, the collection head may be configured to laterally deflect from the distal extension of the slider so that the collection head may be positioned in an appropriate location to maximize collection of biological samples while preventing collection of unwanted cells and/or tissues as well as to prevent any interaction between the collection head and the slider which could otherwise dislodge any collected sample. In some variations, the actuator may include one or more feedback mechanisms (e.g., haptic feedback, light/visual indicators, sound/auditory indicators, a display with notifications, combinations thereof, etc.) to indicate movement of the collection head to the user while inserted into the body, to aid in self-collection.

FIGS. 1A and 1B depict an exemplary variation of a top view of a universal single-handed device 100 for self-collection of a biological sample. FIGS. 1C and 1D depict an exemplary variation of a side view and an exploded view, respectively, of the universal single-handed device 100 for self-collection of a biological sample.

In general, the device 100 comprises a sheath 102 comprising a distal end 103. The distal end 103 of the sheath 102 may be configured for insertion into a user's body. The distal end 103 of the sheath 102 may be configured to transition between a closed configuration (e.g., distal end 103 in FIG. 1A) and an open configuration (e.g., distal end 103 in FIG. 1B). The distal end 103 of the sheath 102 may transition between the open and closed configuration in any suitable manner. For example, in some variations, the distal end of the sheath comprises two or more flexible segments having an opening or slit therebetween, such as for example, flexible distal segment 105a and flexible distal segment 105b, etc. (collectively referred to as "flexible distal segments 105"). In variations in which flexible distal segments are used, an actuator may be used to move apart the flexible segments thus creating an opening in the distal end of the device to expose a collection head 108.

A shaft 104 may be partially disposed, placed, and/or positioned within the sheath 103. The proximal end of the shaft 104 may be coupled to an actuator 106. The distal end of the shaft 104 may be coupled to, attached to, or otherwise affixed to a collection head 108. A handle 110 may be attached to, coupled to, or otherwise affixed to the proximal end of the sheath 103. At least a portion of the shaft 104 and the actuator 106 may be disposed in the handle 110. The handle 110 may include a slot 112. The actuator 106 may be configured to advance, retract, and/or rotate the shaft 104. The shaft 104 may further be coupled to a slider 114 having distal extension 114a, as shown in FIG. 1D. For example, the slider 114 may be mounted on, integrated with, and/or otherwise attached to the shaft 104 via any suitable coupling mechanism (e.g., mechanical coupling such as friction fit, snap fit, etc., and/or magnetic coupling). The distal extension 114a may be configured to hold, house, stabilize, or otherwise support the collection head 108.

FIG. 1A depicts the distal end 103 of the sheath 102 in the closed configuration. As seen in FIG. 1A, in the closed configuration, the actuator 106 may be in an initial resting or first position (e.g., original position before the device 100 has been used). For example, in the variation shown in FIG. 1A, the actuator 106 is in a retracted position such that the actuator 106 is near the proximal end of slot 112. Since the actuator 106 is coupled to the shaft 104, when the actuator is in the retracted position, the shaft 104 (and in variations where a slider is used, the slider) are also in retracted positions. In the retracted position, the collection head 108 may be at least partially enclosed within the sheath 102. For example, the distal end 103 of the sheath 102 may cover the collection head 108. In the closed configuration, the flexible distal segments 105 of the distal end 103 of the sheath 102 may be in close proximity and/or close contact with each other. Accordingly, the close proximity of the flexible distal segments 105 may cause the flexible distal segments 105 to cover the collection head 108 at least partially in the closed configuration.

FIG. 1B depicts the distal end 103 of the sheath 102 in the open configuration. In this variation, the actuator 106 may be advanced within slot 112. For example, the actuator 106 may be advanced toward the distal end of slot 112. Advancing the actuator 106 within the slot 112 may cause the shaft 104, the collection head 108, and the slider 114 to also advance. In variations where flexible distal segments are used, advancement of the shaft 104, collection head 108, and/or the slider 114 causes the flexible distal segments 105 in the distal end 103 of the sheath 102 to flex or part away from each other. When the flexible distal segments 105 flex or part away from each other, an opening is created, thereby exposing the collection head 108 and the distal extension 114a of slider 114. When the actuator 106 has been advanced, the collection head 108 is advanced from the distal end 103 of the sheath 102 to collect the biological samples.

Sheath

Figure 2A:
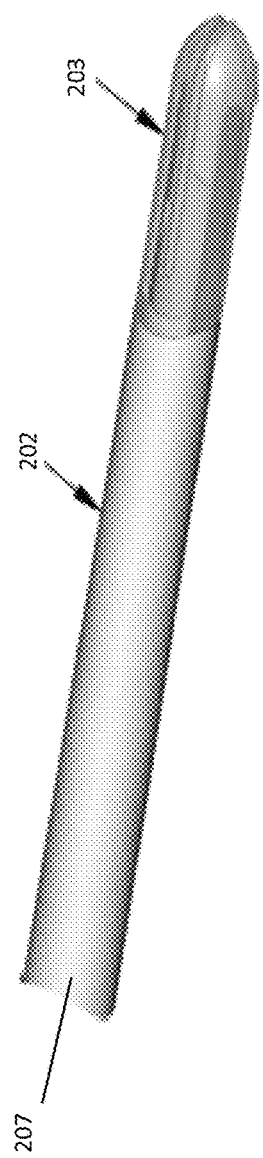
FIG. 2A depicts an exemplary variation of a sheath of a universal single-handed device for self-collection of a biological sample.

As discussed above, the universal single-handed devices described herein may comprise a sheath. FIG. 2A depicts an exemplary variation of a sheath 202 that may be used with the universal single-handed devices described herein. As shown there, sheath 202 comprises a distal end 203, which is configured for insertion into a user's body. The sheath 202 may be of suitable shape, be made of any suitable biocompatible material, and have any suitable size, appropriate for insertion into the user's body. For example, the sheath 202 may be of cylindrical shape, tubular shape, barrel shape, circular longitudinal cross-sectional shape, oval longitudinal cross-sectional shape, elliptical or ellipsoid longitudinal cross-sectional shape, a combination thereof, and/or the like. The sheath may have a uniform or non-uniform cross-sectional size and shape and may or may not taper along its length. In variations in which the device is configured for self-collection of cervical cells and/or tissue, the sheath may have a rounded distal tip similar in the shape to the distal tip of a tampon applicator.

The dimensions of the sheath 202 (e.g., length, weight, density, or rigidity) may be selected as appropriate for the lumen or opening and in each case be configured to be atraumatic to help mitigate damage or disruption to tissues and cells when it is inserted into a user's body.

In variations in which the self-collection device is configured for insertion into a user's vaginal canal, the sheath may have a diameter between about 10 mm and about 40 mm, between about 15 mm and about 35 mm, between about 20 mm and about 30 mm, or between about 22 mm and about 25 mm (including all values and sub-ranges therein). In these variations, the length of the sheath 202 may be between about 100 mm and about 200 mm, between about 120 mm and about 180 mm, and between about 140 mm and about 160 mm (including all values and sub-ranges therein). The sheath 202 may include a lumen to at least partially receive the shaft (e.g., shaft 104) of the device 100. In variations in which the device is configured for insertion into the user's vaginal canal, the diameter of the lumen may be between about 9.5 mm and about 39.5 mm, between about 14.5 mm and about 34.5 mm, between about 19.5 mm and about 29.5 mm, or between about 21.5 mm and about 24.5 mm (including all values and sub-ranges therein). In some variations, the thickness of the walls of the sheath 202 may be between about 0.5 mm and about 4 mm, between about 1 mm and about 3.5 mm, between about 1.5 mm and about 3 mm, or between about 2 mm and about 2.5 mm (including all values and sub-ranges therein).

It should be readily understood that the dimensions of the sheath 202 may be different for different applications or uses of the device 100. More specifically, the dimensions of the sheath 202 may be configured based on the lumen or opening into which the device is to be inserted. For example, when the device is configured for collecting squamous cells from the anus, then the diameter of the sheath 202 may be configured to be suitable for insertion into a user's anal canal. In variations in which the device is configured for insertion into a user's anal canal, the length of the sheath 202 may be between about 100 mm and about 300 mm, between about 150 mm and about 250 mm, or between about 200 mm and about 230 mm (including all values and sub-ranges therein). In such variations, the sheath 202 may include a bend at the distal end 203 for insertion into the user's anal canal.

The devices described herein may be made of any suitable material. In some variations the sheath, actuator, slider, and handle are all made of a single material. In other variations, multiple materials are used. The distal end of the sheath may comprise a biocompatible material. In some variations, the sheath 202 comprises a thermoplastic elastomer such as for example, a polypropylene copolymer. The sheath may comprise one or more lubricious materials, which may take the form of a coating, or may be integral with, impregnated within, or comprise entirely, the sheath material. In some variations, the sheath 202 may comprise silicone.

As discussed above, the sheath 202 may be attached, coupled to, or otherwise integrated with the handle (e.g., handle 110) of the device 100. In some variations, the sheath is integrally formed with the handle. In other variations, the sheath is coupled to the handle via friction fitting, mechanical fitting, magnetic fitting, compression fitting, and the like. In one variation, the proximal end of the sheath 202 includes one or more coupling extensions to couple the sheath 202 to the handle (e.g., handle 110) of the device 100 thus providing a mechanical fitting. For example, the coupling extensions may be mechanical extensions such as for example, mechanical pins, slides, one or more grooves, one of more channels, a combination thereof and/or the like. A counterpart mechanical extension may be positioned on the handle to mechanically couple the sheath 202 to the handle. Additionally, or alternatively, the coupling extensions may be magnetic extensions such as for example, magnetic pins. A corresponding counterpart magnetic pin may be positioned on the handle to magnetically couple the sheath 202 to the handle.

Figure 2C:
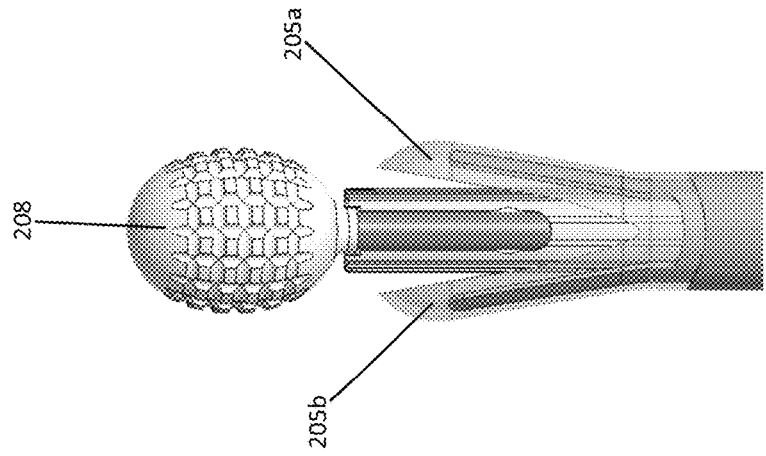
FIG. 2C depicts an exemplary variation of a distal end of a sheath of a universal single-handed device when the distal end is in an open configuration.
Figure 2B:
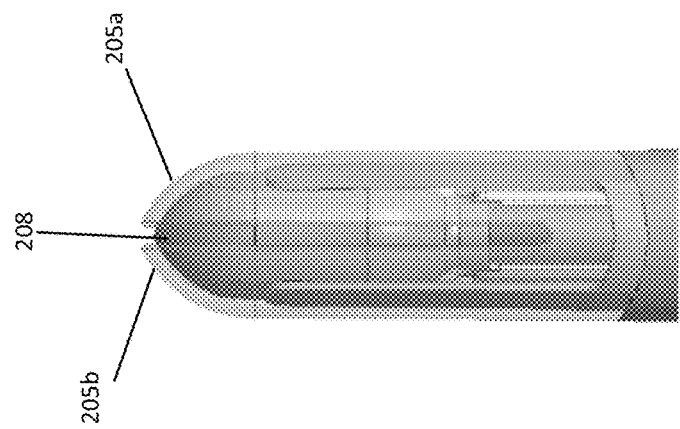
FIG. 2B depicts an exemplary variation of a distal end of a sheath of a universal single-handed device when the distal end is in a closed configuration.

The distal end 203 of the sheath 202 may be configured for insertion into the user's body. FIGS. 2B and 2C depict an exemplary variation of the distal end 203 of the sheath 202. The distal end of the sheath may be formed integral with the rest of sheath 202 or may be coupled or attached to sheath 202. For example, in variations in which the distal end of the sheath is attached or coupled to the rest of the sheath, it may be coupled in any of the manners described above with respect to how the sheath may be coupled to the handle.

The distal end of the sheath is configured to transition between an open configuration and a closed configuration. In this way, the collection head is protected from contamination prior to use and exposed for collection during use. The distal end of the sheath may be configured to provide an open configuration in any suitable manner. For example, the distal end may comprise hinged portions that open and close, retractable portions that may be withdrawn or retraced to expose the collection head, and the like. In some variations, the distal end of the sheath comprises flexible segments that are configured to flex or part away from each other thereby creating an opening, for example, the two or more flexible distal segments 205a 205b, etc. discussed above.

In variations where flexible distal segments are used, they may be formed in any suitable manner. For example, they may be formed by a plurality of slits, slots, or openings formed on the distal end of the sheath 202. The flexible distal segments may have any suitable shape and may comprise the same or different materials than the rest of the sheath. In some variations, the flexible distal segments comprise the same material as the rest of the sheath and are formed by the creation of a plurality of axial slits in the distal end of sheath. In these variations, the distal end 203 may comprise a thermoplastic elastomer such as for example, a polypropylene copolymer, and/or silicone, and/or a lubricous material.

Alternatively, the distal end 203 may be formed from materials different from the sheath 202. In these variations, the distal end may be formed integral with the rest of the sheath or may be attached or coupled to the sheath. For example, the distal end 203 may be formed separate from the sheath 202 and may be of a suitable shape. In such variations, the distal end 203 may include a lumen to receive the collection head and/or a slider for holding, housing, supporting and/or stabilizing the collection head. In variations where the distal end is formed of different materials from the sheath, the distal end 203 may still include flexible distal segments, for example, formed by a plurality of axial splits in the distal end. In such variations, a proximal end of the distal end 203 may be attached to and/or integrated with the distal end of the sheath 202.

As discussed above, the distal end 203 may be configured to transition between an open configuration and a closed configuration. FIG. 2A depicts an exemplary variation of the distal end 203 in closed configuration. In the variation shown there, flexible distal segments 205a and 205b are used to help with the transition. As shown in FIG. 2A, the flexible distal segment 205a and flexible distal segment 205b may be in close proximity to each other. The flexible distal segments 205a and 205b may at least partially enclose the collection head 208 in the closed configuration. While the variation shown here includes two flexible distal segments, it should be understood that any number of flexible distal segments may be used, e.g., two, three, four, five, six, or more.

In the variation shown in FIGS. 2A and 2B, an actuator is used to advance the shaft, collection head, and slider. As the shaft is advanced distally toward the flexible distal segments, force from the shaft is applied to the flexible distal segments from the shaft, collection head, and/or slider, thus forcing the flexible distal segments apart. FIG. 2B depicts an exemplary variation of the distal end 203 in the open configuration. As shown in FIG. 2B, the flexible distal segments 205 have parted or separated from each other by nature of the segments being flexible However, in other variations, the distal segments may include a physical hinge and the distal segments may be configured to pivot away from each other about the hinge.

In variations where flexible distal segments are used, they may further function as a speculum. For example, the flexible distal segments 205 may be configured to align with a portion of the user's lumen into which the device 100 is to be inserted. For instance, if the device 100 is to be inserted in a user's vaginal canal, the flexible distal segments 205 may push the vaginal walls open and may help align the collection head 208 with the user's cervix. Additionally, or alternatively, in some variations, the flexible distal segments 205 may displace tissues surrounding the user's cervix so that the collection head 208 is exposed only to the cervical cells. In some variations, the flexible distal segments 205 may allow the device 100 to self-center in the user's vagina. When the sheath is in the open configuration, it may provide for unhindered movement of the collection head 208. For example, the collection head 208 may be allowed to expand, extend, rotate and/or bend. After use, the collection head may be retracted through the opening and the sheath may be transitioned to its closed configuration, thereby helping to protect the biological sample from contamination or loss. In some variations, the slits, slots, or openings between the flexible distal segments may be such that they may prevent the pinching of tissues surrounding the user's cervix and also prevent prolapse of the tissues surrounding the user's cervix.

In some variations, each of the flexible distal segments 205 have the same dimensions (e.g., length, width, thickness, etc.), and the dimensions may be selected depending on the lumen or opening in which the device is to be used. For example, in variations in which the device is configured for insertion into a user's vaginal canal, the flexible segments may have a length of about 15 mm. In other variations, the length of the flexible distal segments may be about 24 mm. In some variations, the dimensions of one flexible distal segment may be different from one or more of the other flexible distal segments.

Shaft

Figure 3:
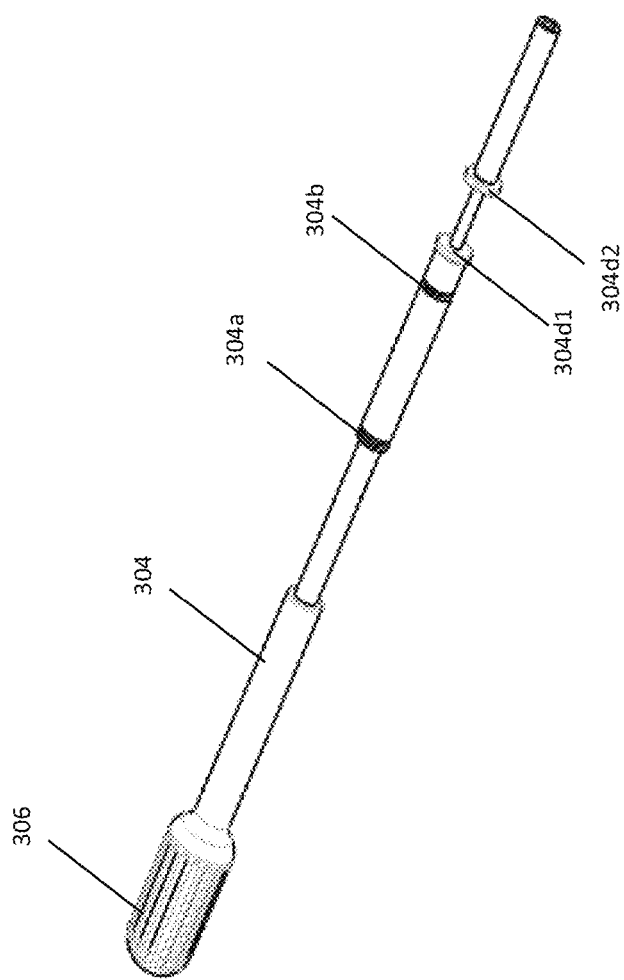
FIG. 3 depicts an exemplary variation of a shaft coupled to an actuator of a universal single-handed device for self-collection of a biological sample.

The devices described here include a shaft having a collection head at its distal end, and at least a portion of the shaft may be received within the sheath. FIG. 3 depicts an exemplary variation of a shaft 304 of the universal single-handed device 100. The shaft 304 may comprise an elongate body having a proximal end and a distal end. The shaft may or may not include a lumen or one or more openings therethrough or therewithin. The shaft may have any suitable cross-sectional shape and dimension. For example, the shaft may have a circular and/or cylindrical cross-sectional shape, may or may not include one or more tapers, and may or may not have a uniform cross-sectional area along its length.

In some variations, the shaft 304 is solid. In some variations, the shaft 304 is hollow. The shaft may be made of any suitable material or materials, and may or may not be made from the same materials as the rest of the device. The shaft may have any suitable dimension, depending on the final application of the collection device and the lumen or opening in which it is to be used. In some variations, the device is configured for insertion into a user's vaginal canal and the length of the shaft 304 may be about 210 mm.

The distal end of the shaft 304 may be connected to, attached to, integrally formed with, or otherwise coupled to (directly or indirectly) a collection head. The proximal end of the shaft 304 may be connected to, attached to, integrally formed with, or otherwise coupled to (directly or indirectly) with an actuator 306. The shaft 304 may be configured to have translational motion, rotational motion, or both. The shaft may transmit rotational motion and/or translational motion from the actuator 306 to the collection head. For example, rotational motion of the actuator 304 may be transmitted to the collection head via the shaft 304, thereby causing the collection head to rotate. Similarly, when the actuator 304 is advanced and/or retracted, the shaft 304 may also advance and/or retract, thereby causing the collection head to advance and/or retract.

In some variations, the shaft 304 may comprise one or more feedback mechanisms to indicate to the user information about a movement of the shaft 304 and consequently movement of the collection head. In this way, better collection of a biological sample may be facilitated. The feedback mechanisms may include any suitable mechanism that may aid the user in collection, including haptic feedback, audible feedback, visual feedback (e.g., lights or information on a display), and the like. In some variations, haptic and audible feedback is provided.

For example, in the variation shown in FIG. 3, the shaft 304 comprises extensions or protrusions 304a and 304b. In this variation, the handle (e.g., handle 110) of the device may include counterpart channels and/or brackets (e.g., channels and/or brackets 404a' and 404b' in FIG. 4 further described below) to receive these extensions or protrusions. For example, the handle may include a first channel and/or bracket (e.g., 404a' in FIG. 4) to receive the extension 304a and a second channel and/or bracket (e.g., 404b' in FIG. 4) to receive the extension 304b. The extension 304a may snap-fit into the first channel and/or bracket and the extension 304b may snap-fit into the second channel and/or bracket. When the shaft 304 rotates and/or translates, the frictional interaction between the channels and/or brackets of the handle and the extensions or protrusions of the shaft 304 may cause a "click" sound and provide haptic feedback to the user. In this way, the user is notified about the amount of rotation and/or translation. For example, a single "click" sound may be indicative of one complete rotation, two simultaneous "click" sounds may be indicative of a translational motion, etc. Additionally, or alternatively, the shaft 304 may comprise one or more stop mechanisms such as for example, stop mechanisms 304d1 and 304d2 to prevent the shaft 304 from advancing or retracting too far.

Actuator

As discussed above, the proximal end of the shaft may be integrally formed with, attached to, connected with, or otherwise coupled to (indirectly or directly) an actuator. The actuator may be any suitable actuator such as for example, a button, roller, knob, pull, slide, any combination thereof, and/or the like, and is configured for universal, single-handed use (e.g., right hand and/or left hand). The actuator 306 may be designed and/or configured to help make the device 100 ergonomic. For example, in one variation the actuator is a roller that is configured to rotate and/or translate and is designed such that a user may use just their thumb to rotate the roller and to advance and/or retract the roller. As discussed above, the actuator may be disposed within a slot (e.g., slot 112) of a handle (e.g., handle 110) of the device. The user may use their thumb to rotate the roller. The roller may rotate within the slot of the handle, thereby causing the collection head (e.g., collection head 108) to rotate. In a similar manner, the user may push the roller with their thumb to advance the roller (e.g., within the slot of the handle). Additionally, the user may use their thumb to pull back or retract the roller (e.g., within the slot of the handle).

In some variations, the roller may be textured (e.g., have a textured coating) or may be formed in a way to provide additional texture (e.g., by including one or more grooves or protrusions) to provide grip when the user uses their thumb to push and/or pull back the roller.

In some variations, the actuator 306 comprises a lock mechanism. In this variation, after the actuator has been actuated, the lock mechanism may lock the actuator 306 in place (e.g., an advanced position). This may help prevent unintentional movement of the actuator 306, for example, backward displacement of the actuator 306. In some variations, the actuator 306 may be fixed on, attached to, coupled to, or otherwise integrated with a gear train. The gear train may comprise one or more gears (e.g., drive gear, follower gear, etc.) that are connected together via a gear chain. For example, the actuator 306 may be fixed on the drive gear that may be connected to a follower gear via a gear chain. The follower gear may be fixed on the shaft (e.g., shaft 304). The gear ratio of the one or more gears may be such that each rotation of the actuator may cause the gears, the shaft, and consequently the collection head to rotate about 4 times, about 5 times, about 6 times, about 7 times, about 8 times, about 9 times, about 10 times, about 11 times, about 12 times, about 13 times, about 14 times, or about 15 times. Such rotational amplification may help ensure that the user rotates the collection head a sufficient number of times in order to obtain enough amount of the biological sample for analysis, thereby enhancing the collection of the biological sample.

In some variations, the actuator 306 may be configured to provide feedback to the user to indicate to the user information about a movement of the actuator 306. For example, the actuator may be configured to provide haptic feedback, audible feedback, visual feedback, combinations thereof, and the like. In some variations, the actuator 306 includes tactile sensors to measure an amount of force applied to the actuator 306. The amount of force may be indicative of a type of movement (e.g., rotation, advancement, retraction) of the actuator 306. Additionally, or alternatively, the amount of force may indicate an amount of movement of the actuator (e.g., amount of rotation, amount of advancement, amount of retraction, etc.). The user may be provided with audible, visual, and/or haptic feedback to indicate the amount of force applied to the actuator 306. For instance, the actuator 306 may be configured to provide visual feedback to the user to indicate to the user information about a movement of the actuator 306. For example, the actuator 306 may include one or more light-emitting diodes (LEDs), or other light sources. The LEDs may be programmed to switch on, switch off, and/or change colors based on the movement of the actuator 306. A user may view the LEDs to identify a type of movement and/or an amount of movement of the actuator 306. In some variations, one or more sensors for collecting data is provided on the actuator, and one or more feedback mechanisms are provided elsewhere on the device for displaying or communicating that and/or other information (e.g., the feedback mechanisms may be on the shaft, the handle, some combination thereof, etc.)

In some variations, the actuator 306 may comprise one or more optical channels. The optical channels may be communicatively coupled to a computing device (e.g., processor(s), computers, tablets, smart phone, etc.) that may be external to, or integrated with the device. For example, the optical channels may be communicatively coupled to the computing device via Bluetooth. The optical channels in the actuator 306 may enable visualization of the actuator, and therefore may provide the user with feedback of the movement of the actuator 306.

The actuator may be made of any suitable material and may or may not be made of the same materials used in other parts of the device. In some variations, the actuator comprises a polymer such as a polypropylene copolymer. The actuator may have any suitable dimensions depending on the type of actuator chosen. In some variations, the actuator is a roller and has a diameter between about 10 mm and about 30 mm, between about 15 mm and about 25 mm, between about 18 mm and about 23 mm, or between about 20 mm and about 22 mm (including all values and sub-ranges therein).

Handle

Figure 4A:
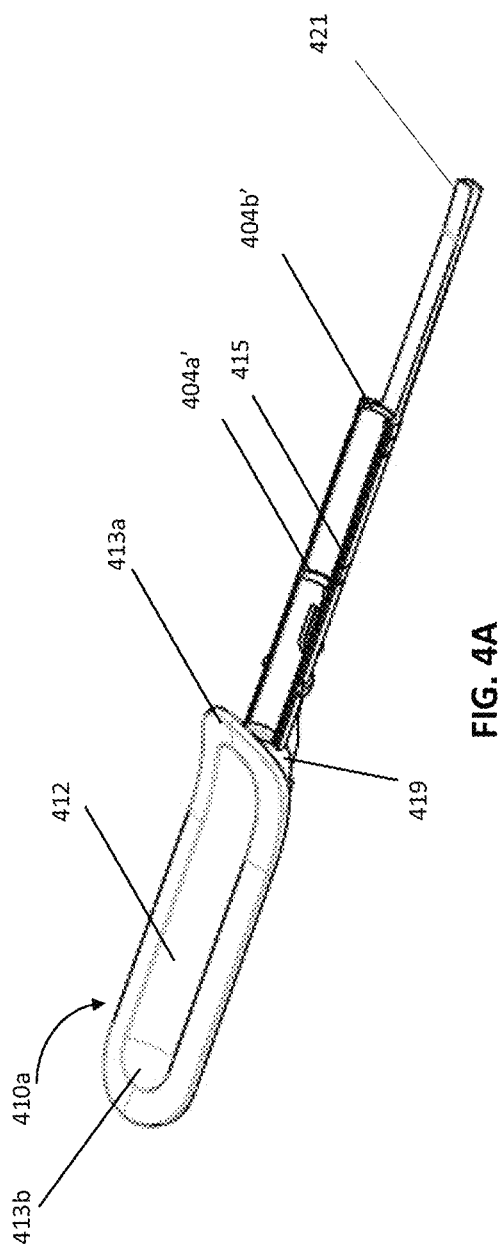
FIG. 4A depicts an exemplary variation of a grip portion of a handle of a universal single-handed device for self-collection of a biological sample.
Figure 4B:
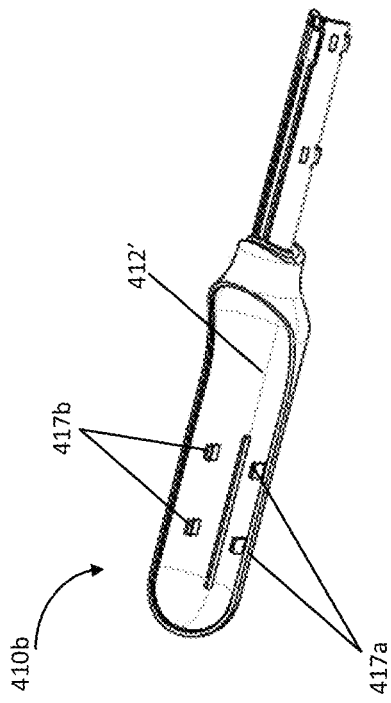
FIG. 4B depicts an exemplary variation of a carriage portion of a handle of a universal single-handed device for self-collection of a biological sample.

The actuator may be disposed within a handle of the device. In some variations, the handle of the device may be configured to receive at least a portion of the shaft. The handle may be formed of a single piece, or more than one piece and coupled together. For example, in some variations, the handle is made from more than one piece and then coupled together to form the handle. For example, FIGS. 4A and 4B depict an exemplary variation of such a device, having a grip portion 410a and a carriage portion 410b. As shown there, grip portion 410a of the handle may include a slot 412 within which an actuator may be disposed (e.g., a roller that may rotate and/or translate). The slot 412 has a distal end 413a and a proximal end 413b. The grip portion 410a may also include a recessed portion 415 to receive a shaft.

In some variations, the distal end 413a of the slot 412 includes an acclivity, or an upward angle. That is, the distal end 413a of the slot 412 may extend from the slot 412 at an angle. In this variation an opening 419 is provided at the distal end 413a of the slot 412, and the shaft may be inserted through that opening. In this variation, a portion of the shaft is positioned within the recessed portion 415 of the grip portion 410a, and the actuator (e.g., actuator 306) may be positioned in the slot 412. The actuator may be configured to advance and retract within the slot 412, and/or rotate within the slot 412. In some variations, the diameter of the actuator and the width of the slot 412 may be such that the actuator fits snuggly within the slot 412 only providing enough room to translate and/or rotate within the slot 412.

In some variations, the grip portion 410a of the handle may include one or more feedback channels and/or brackets such as for example, bracket 404a' and bracket 404b'. As discussed with reference to FIG. 3 above, the shaft 304 may include counterpart feedback extensions or protrusions (such as, for example, extension 304a and extension 304b) that may snap-fit into the brackets 404a' and 404b'. When the shaft 304 rotates and/or translates, the frictional interaction between the channels and/or brackets 404a' and 404b' of the grip portion 410a and the extensions 304a and 304b of the shaft 304 may cause a "click" sound indicative of a movement of the actuator 306 and/or the shaft 304. In some variations, a distal end 421 of the grip portion 410a may include a ramp and/or an incline. The ramp and/or incline 421 may be configured such that the collection head (e.g., collection head 108) advances at an upward angle when advanced from the sheath (e.g., sheath 202).

The grip portion may have any suitable dimensions. In general, the grip portion is configured to provide ergonomic control so that a user may operate the device using only a single hand, and such that either hand of the user may be used. In some variations, a width of the grip portion 410a may be between about 15 mm and about 45 mm, between about 20 mm and about 40 mm, between about 25 mm and about 35 mm, or between about 28 mm and about 30 mm (including all values and sub-ranges therein). In some variations, a length of the grip portion 410a may be about 219 mm In some variations, a total height of the grip portion 410a may be between about 15 mm and about 30 mm, between about 18 mm and about 28 mm, between about 20 mm and about 25 mm, or between about 21 mm and about 23 mm (including all values and sub-ranges therein).

The grip portion 410a of the handle may be coupled to a carriage portion of the handle. FIG. 4B depicts an exemplary variation of a carriage portion 410b of the handle of the device 100. The carriage portion 410b may include a depression 412'. The actuator may be received within the depression 412'. The slot 412 of the grip portion 410a may be aligned with the depression 412' of the carriage portion 410b. The actuator may be configured to rotate and/or translate within both the slot 412 of the grip portion 410a and the depression 412' of the carriage portion 410b. In some variations, the carriage portion 410b may include feedback extensions such as 417a and 417b. The actuator 306 may include grooves such that the feedback extensions 417a and 417b may snap-fit into the grooves of the actuator 306. When the actuator rotates, the frictional interaction between the grooves and the feedback extensions 417a and 417b may cause a "click" sound indicative of a rotational movement of the actuator 306.

The grip portion 410a and the carriage portion 410b may be coupled to, connected, or attached to one other in any suitable way. For example, after the shaft 304 is received within the grip portion 410a of the handle such that the actuator 306 is disposed in the slot 412, the slot 412 may be aligned with the depression 412' of the carriage portion 410b of the handle. The grip portion 410a and the carriage portion 410b may be coupled with each other such that the depression 412' may receive the actuator 306. The slot 412 of the grip portion 410a may expose the actuator 306 for use by the user. The user may hold the carriage portion 410b of the handle such that the user's thumb may be facing the grip portion of the handle 410a. The user's thumb may engage with the actuator 306 via the slot 412 on the grip portion 410a of the handle. The height of the depression 412' in the carriage portion 410b of the handle may be chosen such that the device is ergonomic and/or provides ergonomic control. For instance, the height of the depression 412' in the carriage portion may be such that both a left-handed user and a right-handed user may engage with the actuator 304 during use of the device 100 with ease, and such that the user may only need a single hand to operate the device.

The carriage portion may have any suitable dimensions. In some variations, a height of the carriage portion 410b may be between about 15 mm and about 30 mm, between about 18 mm and about 28 mm, between about 20 mm and about 25 mm, or between about 21 mm and about 23 mm (including all values and sub-ranges therein). In some variations, a width of the carriage portion 410b may be between about 15 mm and about 45 mm, between about 20 mm and about 40 mm, between about 25 mm and about 35 mm, or between about 28 mm and about 30 mm (including all values and sub-ranges therein). In some variations, a length of the carriage portion 410a may be about 166 mm.

While a two-piece handle was described here in detail as one illustrative variation, it should be understood that a handle need not be formed of two pieces and coupled in the manner described. Indeed, the handles for use with the devices described herein may be formed from a single piece, or may be formed from multiple pieces (e.g., two, three, four, five, six, or more pieces). In addition, while audible, visual, and haptic feedback mechanisms were described here in detail, any suitable feedback mechanism may be provided on the handle as described herein throughout.

Slider

Figure 5:
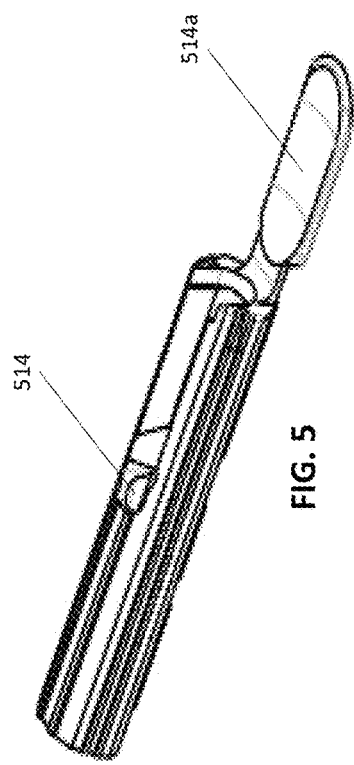
FIG. 5 depicts an exemplary variation of a slider with a distal extension of a handle of a universal single-handed device for self-collection of a biological sample.

In some variations, the device further comprises a slider coupled to a shaft and having an extension at its distal end to hold, house, stabilize, or otherwise support a collection head. FIG. 5 depicts one exemplary variation of a slider 514 with a distal extension 514a. The slider 514 may be integrally formed with the shaft, or may be connected to, attached to, or otherwise coupled to the shaft in any suitable manner. In some variations, the slider 514 is mechanically coupled to the shaft. For example, in this variation, the slider 514 includes one or more elongate channels, and one or more mechanical extensions (e.g., extension 723 in FIGS. 7A and 7B described below) on the shaft may be received within the elongate channels of the slider 514, thereby coupling the shaft to the slider 514. Advancing the shaft may advance the slider 514 and the distal extension 514a. In some variations when flexible distal segments are used on the distal end of the shaft, when the slider 514 and distal extension 514a are advanced, the flexible distal segments (e.g., flexible distal segments 105) may be forced to part from each other, thereby transitioning the distal end (e.g., distal end 103) of the sheath (e.g., sheath 102) into an open configuration.

The slider may be made of any suitable material, and may or may not be made from the same materials as the rest of the device. In some variations, the slider 514 comprises a flexible material. In some variations, the slider is made from a polymer such as polypropylene copolymer. The slider may have any suitable dimensions, depending on the intended application of the device. In some variations, the device is configured for insertion into a user's vaginal canal and the slider has a length between about 40 mm and about 150 mm, between about 60 mm and about 120 mm, between about 80 mm and about 110 mm, or between about 85 mm and about 100 mm (including all values and sub-ranges therein). In some variations, a height of the slider 514 may be about 14 mm.

In some variations, the distal extension 514a is aligned with the collection head (e.g., collection head 108). In some variations, the distal extension 514a houses, holds, stabilizes, or otherwise supports the collection head. In the closed configuration, the collection head supported by the distal extension 514a may be at least partially enclosed in a distal end (e.g., distal end 103) of a sheath (e.g., sheath 102). In the open configuration, there is an opening in the distal end of the sheath (e.g., caused by separation of flexible distal segments) allowing for the advancement of the distal extension 514a and the collection head from the sheath.

In some variations, the distal extension 514a may be configured to help guide the collection head to a target zone for the collection of the appropriate biological samples. For example, if the device is configured for collecting cervical cells of a user, then the distal extension 514a may be configured to deflect the posterior wall of the vagina. This may prevent the collection head from collecting vaginal cells. Additionally, the distal extension 514a may be configured to occupy a cavity (e.g., a fornice/fornix) within a user's body such that the collection head may be positioned to appose the portion in the user's body from which the biological sample is to be collected. For instance, if the biological sample is cervical cells, then the distal extension 514a may be configured to occupy the vaginal fornix to position the collection head adjacent to the cervix in order to help in the collection of cervical cells while reducing the probability that other unwanted cells are also collected. Furthermore, the distal extension 514a may be configured to allow the collection head to expand and rotate without inward pressure from surrounding tissues.

The distal extension may have any suitable dimensions. In variations where the device is configured for insertion into a user's vaginal canal the distal extension 514a may have a length between about 20 mm and about 50 mm, between about 25 mm and about 45 mm, between about 30 mm and about 40 mm, or between about 35 mm and about 38 mm (including all values and sub-ranges therein).

Collection Head

The devices described here include a collection head for collecting a biological sample. The collection head may attached to, positioned on, mounted on, coupled to, or otherwise integrated with a distal end of the shaft of the device. For example, the collection head may comprise a stem on the proximal end that may be attached to, positioned on, mounted on, or otherwise integrated with the distal end of the shaft. The collection head may be made from any suitable biocompatible material and may be configured to be atraumatic so that damage to surrounding tissues are reduced while the biological sample is being collected from the user's body. For example, the collection head may comprise materials such as collagen-based cryogel, silicone, polyurethane, and/or the like. The collection head may have any suitable shape and/or geometry and take any form, e.g., a brush, a sponge, a bristle, a protrusion, and/or the like.

Figure 6B:
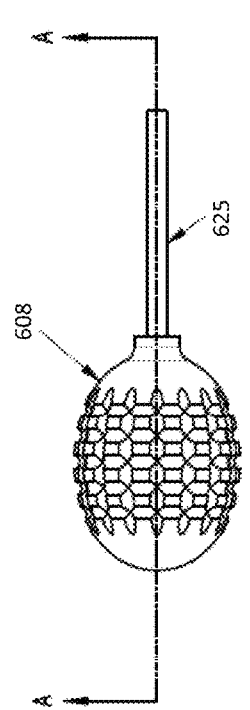
FIG. 6B depicts an exemplary variation of the cross-sectional view of the collection head depicted in FIG. 6A.
Figure 6D:
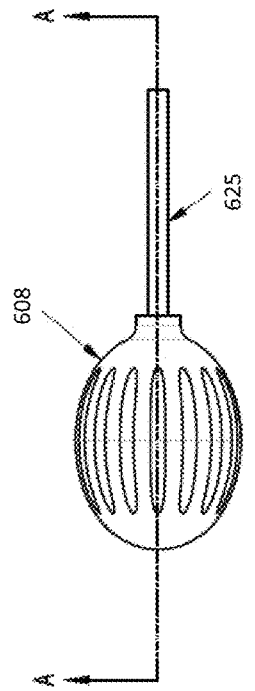
FIG. 6D depicts an exemplary variation of the cross-sectional view of the collection head depicted in FIG. 6C.
Figure 6A:
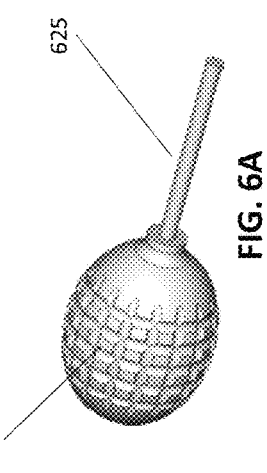
FIG. 6A depicts an exemplary variation of a collection head of a universal single-handed device for self-collection of a biological sample.
Figure 6C:
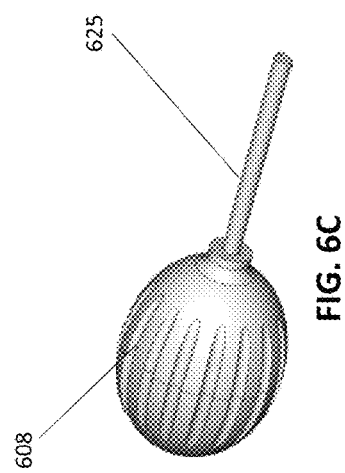
FIG. 6C depicts an exemplary variation of a collection head of a universal single-handed device for self-collection of a biological sample.

FIG. 6A provides an illustrative variation of a suitable collection head 608 and FIG. 6B depicts a cross-sectional view of the collection head shown in FIG. 6A. FIG. 6C provides an illustrative variation of another suitable collection head 608 and FIG. 6D depicts a cross-sectional view of the collection head shown in FIG. 6C. In the variations shown there, the collection head 608 is generally in the form of an orb-like sponge. The collection head 608 may be configured to hold onto and/or retain any biological sample that it may have collected. In some variations, the collection head 608 may comprise one or more surface indentations. The surface indentations may enable at least a segmentation of the collection head 608 to engage with a target part (e.g., cervical os) of the user's body. The surface indentations may also enable the collection head to have spaces and/or pores to collect and/or entrap biological samples. For instance, as seen in FIG. 6A, the collection head 608 may comprise an open cell lattice pattern and/or a honeycomb design pattern. For example, the collection head may be formed with an integrated open cell lattice pattern and/or honeycomb pattern. Additionally, or alternatively, the open cell lattice pattern and/or the honeycomb pattern may be formed separately from the collection head. The open cell lattice pattern and/or the honeycomb pattern may then be attached to a sponge to form the collection head 608. The open cell lattice pattern and/or the honeycomb pattern may be made of the same material as the sponge. Alternatively, the open cell lattice pattern and/or the honeycomb pattern may be made of a different material from the sponge. In some variations, as seen in FIG. 6C, the collection head 608 may comprise a corrugated pattern, and/or laser-etched ridges. For example, corrugated patterns and/or laser-etched ridges may be formed on the orb-like sponge, thereby forming the collection head 608. The surface indentations on the collection head 608 may allow the collection head 608 to compress and expand to its natural size more easily.

Although, FIGS. 6A-6D depict the collection head in the form of an orb-like sponge, the collection head may have any suitable shape and/or geometry. For example, the collection head 608 may be a square, circular, rectangular, oval, triangular, cone-like, or polygon cross-sectional shape, etc. In some variations, the collection head may be in the form of a cone-like sponge. As noted above, the collection head 608 may also be made from any suitable biocompatible material. In some variations, the collection head comprises polyurethane, for example, reticulated polyurethane. The density of the collection head 608 may be between about 10 ppi and about 90 ppi, between about 20 ppi and about 80 ppi, between about 30 ppi and about 70 ppi, between about 40 ppi and about 60 ppi, or between about 45 ppi and about 50 ppi (including all values and sub-ranges therein). Generally, if the collection head has a lower density, then the collection head may be configured to collect more biological sample. However, collection heads with lower density may not compress easily. On the other hand, a collection head with higher density may compress and expand to its natural size more easily.

The collection head 608 may have any suitable dimensions depending on the intended use of the device and the lumen or opening in which it is to be used. In some variations, the device is configured to be inserted into a user's vaginal canal and the collection head 608 together with its supporting stem has a length between about 30 mm and about 90 mm, between about 35 mm and about 85 mm, between about 40 mm and about 80 mm, between about 45 mm and about 75 mm, between about 50 mm and about 70 mm, between about 55 mm and about 65 mm, or between about 58 mm and about 62 mm (including all values and sub-ranges therein). In some variations, a height of the collection head 608 may be about 22 mm.

In some variations, the collection head 608 may include biological probes for binding or detecting biological targets (e.g., molecular epitopes, cells, microbes, viruses, nucleic acids, etc.). The biological probes may facilitate sample collection or even undergo a reaction, such as for example, chemical, optical, voltage, conformational shape, and/or the like to generate an in situ signal if it comes into contact with a selected biological target. In some variations, the collection 608 head may be configured to vibrate when it comes into contact with a selected biological target.

The collection head 608 may be attached to or otherwise integrated with a stem 625 on its proximal end. For example, the collection head 608 may include a lumen or an opening in its proximal end to receive the stem 625. The stem 625 may have any suitable cross-sectional shape and dimension. The stem 625 may have a circular and/or cylindrical cross-sectional shape. In some variations, the stem 625 is solid. In some variations, the stem 625 is hollow. The stem may be made of any suitable material or materials, and may or may not be made from the same materials as the rest of the device. The stem 625 may have any suitable dimension, depending on the final application of the collection device 608 and the lumen or opening in the proximal end of the collection device 608. In some variations, the device is configured for insertion into a user's vaginal canal and the length of the stem 625 may be between about 25 mm and about 75 mm, between about 30 mm and about 70 mm, between about 35 mm and about 65 mm, or between about 40 mm and about 60 mm (including all values and sub-ranges therein). In such variations, a diameter of the stem 625 may be about 2.5 mm. The proximal end of the stem 625 may be connected to, attached to, integrally formed with, or otherwise coupled to (directly or indirectly) a shaft of the devices described herein.

In some variations, the collection head is configured to be in a compressed state when not in use and an expanded state when in use. In the expanded state, the collection head is expanded and may touch all biological surfaces of the portion of the user's body from which the biological sample is to be collected. In the compressed state, the collection head is compressed and retracted into the sheath. FIG. 7A depicts an exemplary variation of a collection head 708 in a compressed state. For example, FIG. 7A depicts the collection head 708 when an actuator (e.g., actuator 106 of device 100) is in its resting retracted toward the proximal end of the handle). More specifically, FIG. 7A depicts the collection head 708 when a distal end (e.g., distal end 103) of a sheath (e.g., sheath 102) of the device (e.g., device 100) is in a closed configuration. As shown in FIG. 7A, in this variation, the collection head is at least partially surrounded by the distal end of the sheath (e.g., flexible distal segments 105). Additionally, or alternatively, as the collection head 708 in this variation is supported by distal extension 714a of a slider, the collection head may be sandwiched between the flexible distal segments and the distal extension 714a of the slider. For example, the top portion of the collection head 708 may be at least partially surrounded by the flexible distal segments and the bottom portion of the collection head 708 may be covered by the distal extension 714a. Extension 723 of the shaft (e.g., shaft 104) of the device may be received in a channel of the slider causing the collection head 708 and its supporting stem 725 to be aligned with a longitudinal axis of the device.

FIG. 7B depicts an exemplary variation of the collection head 708 in an expanded state. FIG. 7B depicts the collection head 708 when an actuator (e.g., actuator 106 of device 100) is in an advanced position. More specifically, FIG. 7B depicts the collection head 708 when a distal end (e.g., distal end 103) of a sheath (e.g., sheath 102) of the device is in an open configuration. As shown in FIG. 7B, in this variation, the distal end of the sheath is open (e.g., by separation of flexible distal segments 105) thereby allowing the collection head to advance in an unhindered manner. The distal extension 714a of the slider that supports the collection head 708 may also be advanced. In this configuration, the extension 723 of a shaft (e.g., shaft 104) of the device may advance such that the extension 723 engages with the ramp 721 (e.g., ramp 421 in FIG. 4A) of a grip portion (e.g., grip portion 410a) of a handle (e.g., handle 110) of the device 100. This may cause the collection head 708 and the supporting stem 725 to laterally deflect from the distal extension 714a of the slider. This lateral deflection may allow the collection head 708 to be positioned apposed against or adjacent to the portion of the user's body from which the biological sample is to be collected. For example, when the device is configured to collect cervical cells, the lateral deflection may position the collection head adjacent to the cervix. In some variations, the lateral deflection may additionally or alternatively create a clearance between the collection head 708 and the distal extension 714a. This may prevent loss of the biological sample onto the distal extension 714a.

Kits

In some variations, the universal single-handed devices described herein may be combined with additional items to form a kit or a system. For example, in some variations, the kit of system may comprise a universal single-handed device (e.g., a universal single-handed device with any combination of features described herein) and a vial. The kit or system may further comprise a cleanser, e.g., alcohol wipes, and/or cleaning liquids, foams, tablets or powders (such as effervescent tablets or powders), or gels (such as water based anti-bacterial foam, liquid, or gel containing, for example, alcohol) and/or instructions for use. In some variations, the system or kit may comprise a plurality of universal single-handed devices (e.g., two, three, or more) and/or a plurality of vials (e.g., two, three, four, or more). In these variations, the kits or systems may be designed to have the user collect biological samples from different portions of the user's body or to collect biological samples from the same portion of the user's body, but at multiple time points.

Figure 8:
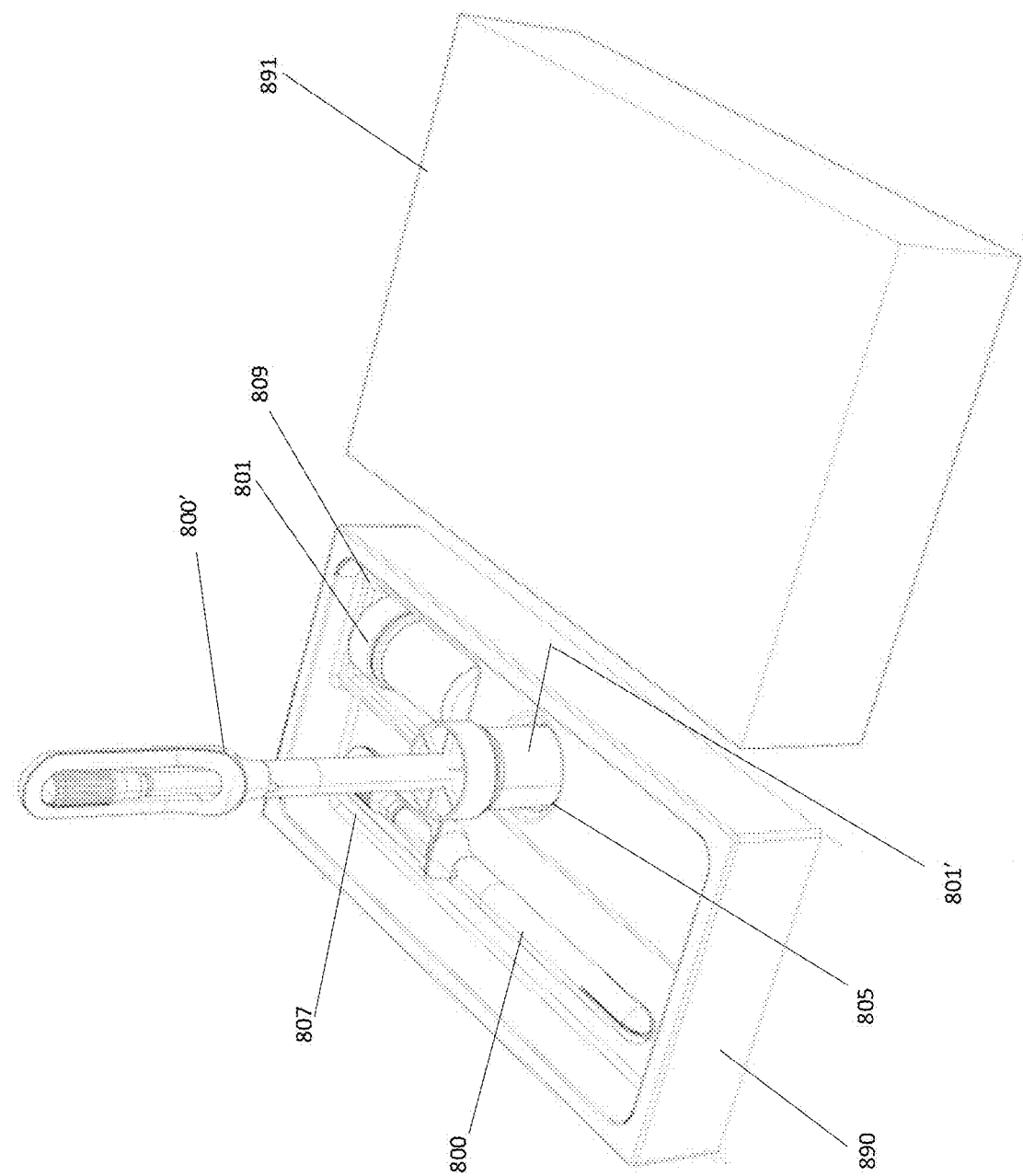
FIG. 8 depicts an exemplary variation of a kit comprising a universal single-handed device for self-collection of a biological sample.

FIG. 8 depicts an exemplary variation of a kit comprising a universal single-handed device 800 as described herein. The kit may be packaged in a frame or kit housing 890. The frame 890 may include a first cavity 807 to receive the universal single-handed device 800. The frame 890 may also include a second cavity 809 to receive a vial 801. Once the vial 801 is placed in cavity 809 and the universal single-handed device 800 is placed in cavity 807, a protective covering 891 may be fitted onto the frame 890 so as to package the kit. In some variations, the protective covering 891 may be a box sleeve with a hollow inside. In such variations, the protective covering 891 may be configured to wrap around the frame 890. In other variations, the protective covering 891 may be a frame cover configured to receive the frame 890. In such variations, the frame 890 may be received within the frame cover 891 such that the frame 890 snugly fits in the frame cover 891. The protective covering 891 may protect the universal single-handed device 800 and the vial 801 from contamination and damage. The frame 890 may comprise the same or different material as protective covering 891.

In some variations, the frame 890 may also include a third cavity 805 that is designed to hold the vial 801 in an upright position. For example, the frame 890 may include the third cavity 805 that may be configured to hold the vial 801 in an upright position (e.g., upright position 801'). In particular, the diameter of the cavity 805 may be designed such that the vial 801 fits in the cavity tightly when it is in upright position 801. When the biological sample is collected, the cavity 805 may hold the vial 801' such that the universal single-handed device 800' is inserted in an upright position into the vial 801' to collect the biological sample. The cavity 805 may provide stability to the vial 801' when the vial is in an upright position. This may prevent the vial 801' from tipping or falling and may avoid spillage of the biological sample when the sample is being collected.

Vial

Figure 9B:
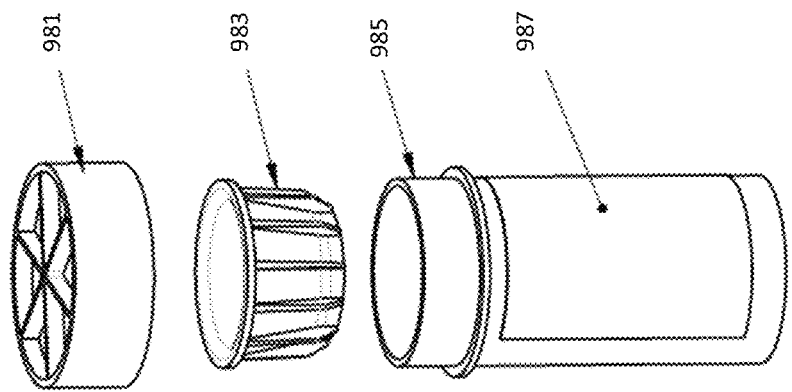
FIG. 9B depicts an exemplary variation of an exploded view of the vial in the kit in FIG. 9A.
Figure 9A:
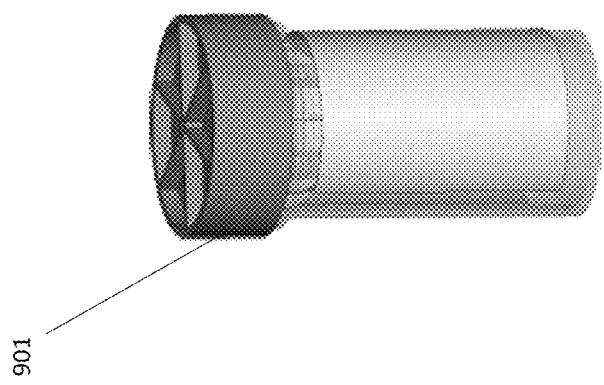
FIG. 9A depicts an exemplary variation of a vial in a kit comprising a universal single-handed device for self-collection of a biological sample.

FIG. 9A depicts an exemplary variation of a vial and FIG. 9B depicts an exploded view of an exemplary variation of a vial. In the variation shown there, vial 901 may comprise a vial body 985, a vial cap 981, a vial adapter 983, and a vial label 987. The vial body 985 may be designed to store the biological sample. The vial body 985 may have any suitable shape. In some variations, the exterior of the vial body 985 may have a cylindrical cross-section, a rectangular cross-section, a circular cross-section, an oval cross-section, and/or the like. In some variations, the interior of the vial body 985 may have the same and/or similar cross-section and/or shape as the exterior of the vial body 985. In some variations, the interior of the vial body 985 may have a different cross-section and/or shape from the exterior of the vial body 985. In some variations, the interior of the vial body 985 may have a funnel-shaped cross section. The funnel-shaped cross-section may guide the universal single-handed device into the vial body 985 for collection of the biological sample. Additionally, or alternatively, after the biological sample has been collected, the funnel-shaped cross-section may compress the collection head of the universal single-handed device so as to drain any additional fluid and/or biological sample from the collection head as the universal single-handed device is being retracted from the vial body 985. In some variations, the vial body 985 may have a diameter that may be greater than the diameter of the collection head in its expanded state. The vial body 985 may comprise any suitable material such as for example, thermoplastics such as polypropylene, or borosilicate glass, etc.

A vial label 987 may be attached to the exterior of the vial body 985. In these variations, for example, at least a portion of the vial label 987 may include an adhesive configured to attach the vial label 987 to the vial body 985. In some variations, the vial label 987 may comprise biaxially-oriented polypropylene, flexible vinyl, etc.

The top portion of the vial body 985 may be configured to receive the vial adapter 983. The vial adapter 983 may be configured to guide a distal end (e.g., distal end 203) of the universal single-handed device into the vial body 985. The vial adapter 983 may comprise any suitable shape, for example, a shape that complements and/or corresponds to the shape of the vial body 985. For example, if the vial body 985 has cylindrical cross-section, then the vial adapter 983 may have a cylindrical and/or a circular cross-section. The vial adapter 983 may be designed such that the top portion of the vial adapter 983 tightly fits within the top portion of the vial body 985. In particular, the diameter of the top portion of the vial adapter 983 may be such that the top portion of the vial adapter 983 snugly fits within the top portion of the vial body 985. In some variations, the vial adapter 983 may be designed such that the bottom portion of the vial adapter 983 may be tapered. The tapered portion of the vial adapter 983 may be configured to guide the collection head into the vial body 985. For example, the distal portion of the universal single-handed device may be inserted into the vial body 985 through the vial adapter 983. In particular, the distal portion of the universal single-handed device in its closed configuration may be inserted into the vial body 985 via the vial adapter 983. To collect the biological sample, the distal portion of the universal single-handed device may be transitioned to its open configuration. The tapered portion of the vial adapter 983 may be designed such that flexible distal segments (e.g., flexible distal segments 205) of the distal end of the universal single-handed device may push against the tapered portion of the vial adapter 983 when the distal end is in the open configuration. The tapered portion may hold the flexible distal segments such that the collection head may be guided to the bottom of the vial body 985 to collect the biological sample. In some variations, the tapered portion of the vial adapter may comprise one or more slits or openings. When the universal single-handed device is retracted from the vial, the slits or openings of the vial adapter may compress the collection head, thereby draining addition fluid and/or biological sample from the collection head. In some variations, the vial adapter 983 may comprise a vent. The vial adapter 983 may comprise any suitable material that does not provide a contamination risk. In some variations, the vial adapter 983 is made of silicone.

The vial cap 981 may act as a stopper and/or seal to protect the content within the vial body 985. The vial cap 981 can be opened to receive the universal single-handed device. Once the biological sample is collected in the vial body 985, the vial cap 981 can be closed to seal the biological sample within the vial body 985. The vial cap 981 may include a locking mechanism (e.g., a childproof lock) to seal the biological sample within the vial body 985 and to prevent spillage of the biological sample. The vial cap 981 may comprise one or more polymers that may be resistant to high temperatures such as, for example, silicones, Polytetrafluoroethylene (PTFE), Polychlorotrifluoroethylene (PCTFE), Fluorinated ethylene propylene (FEP), etc. The polymers may be resistant to damages that may be caused by one or more preservatives that may be in the vial.

In some variations, the vial 901 may include one or more preservatives such as for example, methanol, ethanol, etc. to store the biological sample. Additionally, and/or alternatively, the vial 901 may include one or more reagents to analyze the biological sample.

FIGS. 10A-10C illustrate an exemplary variation of collecting a biological sample in a vial (e.g., vial 901) using a universal single-handed device described herein. In FIG. 10A, a distal end 1003 (e.g., similar to distal portion 103) of a sheath 1002 (e.g., similar to sheath 102) universal single-handed device may be advanced into a vial comprising a vial adapter 1083 and a vial body 1085. In FIG. 10B, the distal end 1003 may be inserted via the vial adapter 1083 into the vial body 1085. The distal end 1003 of the sheath 1002 may be in the closed configuration. As discussed above, in the closed configuration, the collection head may be covered by the distal end 1003. In FIG. 10C, the user may actuate the actuator to transition the distal end 1003 of the sheath 1002 from the closed configuration to an open configuration. The flexible distal segments 1005 (e.g., similar to flexible distal segments 105) may part from each other in the open configuration. The flexible distal segments may push against the tapered portion of the vial adapter 1083. The vial adapter 1083 may hold the flexible distal segments 1005 such that the collection head 1008 is aligned and held in the bottom portion of the vial body 1085 to collect the biological sample.

FIGS. 11A and 11B depict another variation of a vial suitable for use with the devices, kits, and methods described herein. FIG. 11A depicts an exploded view of the vial, while FIG. 11B depicts a partially assembled view. As shown there, vial 1101 may comprise a sample vial body 1185, a shell vial body 1186, a vial cap 1181, a vial adapter 1183, and a seal 1184. The sample vial body 1185 may be designed to store the biological sample and may be similar to the vial body described elsewhere herein (e.g., vial body 985 in FIG. 9). For example, in some variations, the sample vial body 1185 may have a funnel-shaped cross-section that may guide the universal single-handed device into the sample vial body 1185 for collection of the biological sample. The funnel-shaped cross-section may also compress the collection head of the universal single-handed device so as to drain any additional fluid and/or biological sample from the collection head as the universal single-handed device is being retracted from the sample vial body 1185. The sample vial body 1185 may comprise any suitable biocompatible material such as for example, thermoplastics such as polypropylene, or borosilicate glass, etc.

In some variations, the sample vial body 1185 may include one or more preservatives such as for example, methanol, ethanol, etc. to store the biological sample. Additionally, and/or alternatively, the sample vial body 1185 may include one or more reagents to analyze the biological sample. The sample vial body 1185 may contain the preservatives and/or reagents such that the preservatives and/or reagents fill up the sample vial body 1185 up to a maximum preservative height. For example, the preservatives and/or reagents may fill up the sample vial body 1185 from the bottom of the sample vial body 1185 to a predetermined preservative height. The preservatives and/or reagents may be prefilled in the vial, or may be filled in the vial by the user.

After the sample vial body 1185 has been filled with the preservative and/or reagent, the sample vial body 1185 may be sealed. For example, the top portion of the sample vial body may receive a vial adapter 1183 that may be similar to the vial adapters described herein (e.g., vial adapter 983 in FIG. 9). As discussed above, vial adapter 1183 may be designed such that the top portion of the vial adapter 1183 tightly fits within the top portion of the sample vial body 1185 and the bottom portion of the vial adapter 1183 may be tapered. A bottom portion of the vial adapter 1183 comprising the tapered portion may include a seal and/or a membrane 1184. Any suitable seal such as an ultrasonic seal, a thermal seal, and/or the like may be attached, coupled to, or otherwise integrated with the bottom portion (e.g., a bottom surface) of the vial adapter 1183. In some variations, the seal 1184 may snugly fit into the tapered portion of the via adapter 1183. The vial adapter 1183 with the seal 1184 may seal the preservatives and/or reagents in the sample vial body 1185 and may protect the sample vial body 1185 from outside contamination. In some variations, the seal may be configured to be ruptured (e.g., torn, broken, etc.) when the universal single-handed device for self-collection is inserted into the sample vial body 1185 for collecting the biological sample.

The sample vial body 1185 may be received in the shell vial body 1186. The shell vial body 1186 may form a protective covering over the sample vial body 1185. The shell vial body 1186 may prevent contents of the sample vial body 1185 from spilling. After the biological sample has been collected, the shell vial body 1186 may provide additional protection to the biological sample, for example, helping to prevent contamination and/or spillage. The shell vial body 1186 may have a length greater than the length of the sample vial body. In some variations, the shell vial body 1186 has a length that is greater than the length of the universal single-handed device for self-collection. In some variations, the shell vial body 1186 has a length greater than the length of a sheath of the universal single-handed device for self-collection. In some variations, the shell vial body 1186 and the sample vial body 1185 have the same length.

The shell vial body 1186 may have any suitable shape, for example, a shape that complements and/or corresponds to the shape of the sample vial body 1185. For example, if the sample vial body 1185 has cylindrical cross-section, then the shell vial body 1186 may have a cylindrical and/or a circular cross-section. In some variations, a bottom portion of the shell vial body 1186 may be slightly tapered. For example, a diameter of a top portion of the shell vial body 1186 may be greater than a diameter of a bottom portion of the shell vial body 1186. Therefore, when the shell vial body 1186 receives the sample vial body 1185, the greater diameter in the top portion allows the sample vial body to be inserted into the shell vial body 1186 with ease. The smaller diameter in the bottom portion may allow the sample vial body 1185 to be tightly held in an upright position by the shell vial body 1186, thereby avoiding tipping of the sample vial body 1185 and/or spillage of contents from the sample vial body 1185.

Therefore, the shell vial body 1186 may be designed such that the bottom portion of the sample vial body 1185 tightly fits within the bottom portion of the shell vial body 1186. In particular, the diameter of the bottom portion of the shell vial body 1186 may be such that the bottom portion of the sample vial body 1185 snugly fits within the bottom portion of the shell vial body 1186.

The vial cap 1181 may act as a stopper and/or seal to protect the contents within the vial. The vial cap 1181 can be opened to receive a universal single-handed device. Once the biological sample is collected in the sample vial body 1185, the vial cap 1181 can be closed to seal the biological sample within the vial. In some variations, the vial cap 1181 may be similar to the vial caps described herein throughout (e.g., vial cap 981 in FIG. 9).

Figure 12E:
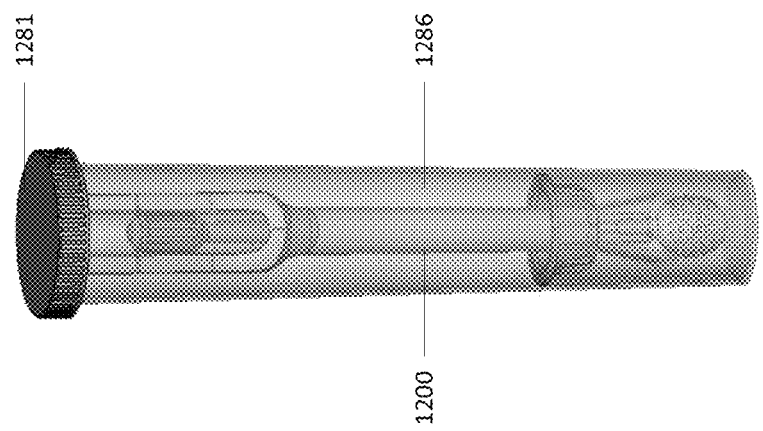

FIGS. 12A-12E illustrate an exemplary variation of collecting a biological sample in a vial (e.g., vial 1101) using a universal single-handed device described herein. In FIG. 12A, after the user collects the biological sample using the universal single-handed device, the user may open the vial cap 1281 to store the biological sample. In FIG. 12B, the user may advance the universal single-handed device into a shell vial body 1286. As described with reference to FIGS. 11A and 11B, the shell vial body 1286 may hold a sample vial body 1285. The vial adapter 1283 of the sample vial body may include a seal in the bottom tapered portion to seal the preservative and/or reagents in the sample vial body 1285. As the universal single-handed device is advanced into the sample vial body 1285 via the vial adapter 1283, the universal single-handed device may rupture the seal in the bottom tapered portion. For example, a distal end 1203 (e.g., similar to distal portion 103) of a sheath 1202 (e.g., similar to sheath 102) of the universal single-handed device may rupture the seal. In some variations, the user may apply a small force in the downward direction while advancing the universal single-handed device to rupture the seal. In FIG. 12C, the distal end 1203 may be inserted via the vial adapter 1283 into the sample vial body 1285. The distal end 1203 of sheath 1202 may be in the closed configuration. As discussed above, in the closed configuration, the collection head may be covered by the distal end 1203. In FIG. 12D, the user may actuate the actuator to transition the distal end 1203 of the sheath 1202 from the closed configuration to an open configuration. In the variation shown here, flexible distal segments 1205 (e.g., similar to flexible distal segments 105) part from each other in the open configuration. The flexible distal segments push against the tapered portion of the vial adapter 1283. The vial adapter 1283 may hold the flexible distal segments 1205 such that the collection head 1208 is aligned and held in the bottom portion of the sample vial body 1285 to collect the biological sample.

After collecting the biological sample, the user may seal the vial using vial cap 1281. In some variations, the user may retract the universal single-handed device 1200 after the biological sample has been collected. In other variations, the user may seal the shell vial body 1286 with the universal single-handed device (or a portion thereof) still therewithin, as shown in FIG. 12E. This variation may prevent unwanted loss of the collected biological sample (e.g., during retraction of the universal single-handed device).

Methods

Figure 13:
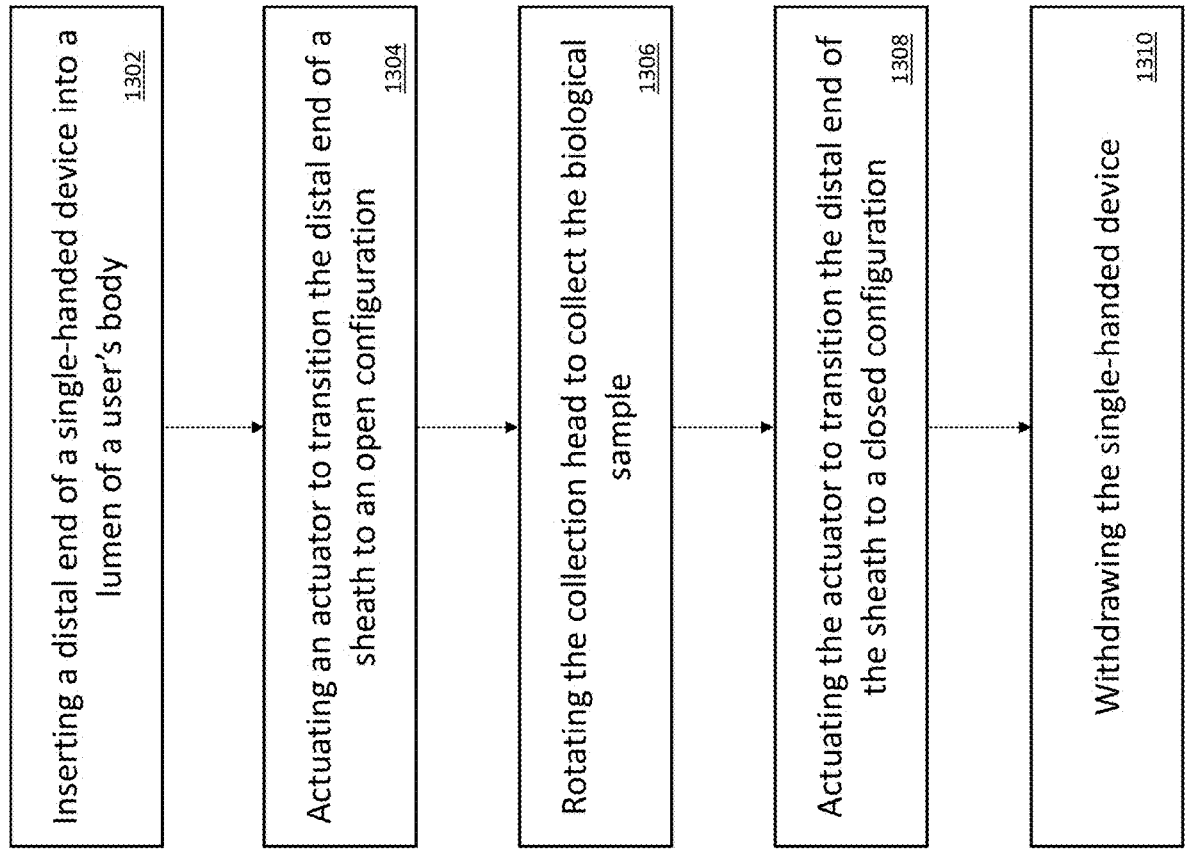
FIG. 13 is a flow chart depicting an exemplary variation of a method for self-collecting a biological sample using the universal single-handed devices described herein.

The devices described herein throughout may be used for self-collection of a biological sample. The devices may be sized and configured depending on their intended use as described herein throughout. For example, the devices may be used for self-collection of bodily tissues (e.g., various cells, etc.), bodily fluids (blood, secretions, etc.), or a combination thereof, and/or the like. For instance, the devices may be used for self-collection of cervical cells, cervicovaginal fluid, menstrual blood, interstitial fluid, cervical secretions, semen, fetal tissue, trophoblast cells, placental tissue, reproductive cells, endometrial cells, and/or the like. They may be used in any body opening or lumen where self-collection of tissue cells or bodily fluids is desired. For example, the devices described herein throughout may be used for self-collection of tissue cells or bodily fluids from a user's vaginal canal, anus, bowels, biliary ducts, throat, ear, and/or the like FIG. 13 provides a flow chart depiction of an exemplary variation of a method for self-collecting a biological sample using the universal single-handed devices described herein. At 1302, the method may include inserting a distal end of the single-handed device into lumen of the user's body. As discussed above, the single-handed device may include a handle that may be attached to and/or coupled to a sheath. The distal end may be configured to transition between an open configuration and a closed configuration. For example, when the device includes flexible distal segments, they may be configured to part from each other, and be separated in the open configuration. In the closed configuration, the collection head may be at least partially covered by the distal end of the sheath (or when used, flexible distal segments). Inserting the distal end may include the user holding the handle of the device in a single hand. The handle may be held such that the user wraps their palm around the handle and place their thumb in close proximity to the actuator of the single-handed device.

At 1304, the method may include actuating an actuator to transition the distal end of the sheath into an open configuration. For example, in some variations, the actuator is a roller and the roller is slidable and rotatable in a slot of the handle. In these variations, the user may place their thumb on the actuator and advance the actuator along the slot of the handle. Advancing the actuator may advance the shaft, collection head, and distal extension of the slider to transition the distal end of the sheath to an open configuration (e.g., by forcing apart flexible distal segments). In some variations, flexible distal segments are used, and the flexible distal segments in the open configuration are configured to function as a speculum. The flexible distal segments may also be configured to push against the walls of the lumen.

The collection head and the distal extension may be advanced from the sheath. The collection head may be advanced such that the collection head laterally deflects from the distal extension of the slider. This may position the collection head so that it is apposed against, or adjacent to, the portion of the user's body from which the biological sample is to be collected. Additionally, when flexible distal segments are used, they may be configured to align with the portion of the user's body from which the biological sample is to be collected.

At 1306, the method may include rotating the collection head to collect the biological sample. For example, the user may rotate the actuator thereby causing rotation of the collection head. At 1308, the method may include retracting the actuator to retract the collection head into the sheath. In variations where flexible distal segments are used, the flexible distal segments may cover at least a portion of the collection head once the collection head has been retracted. At 1310, the method may include withdrawing the single-handed device from the lumen of the user.

In some variations, the method may optionally include advancing the distal end of the sheath into a vial for collecting the biological sample. The distal end may be inserted via a vial adapter into a vial body when the distal end of the sheath is in its closed configuration. The method may optionally include actuating the actuator to transition the distal end of the sheath to the open configuration. The flexible distal segments of the distal end may push against the walls of the vial adapter and the collection head may be aligned to the bottom portion of the vial body in the open configuration. The biological sample from the collection head may be transferred into the vial body. The method may optionally include storing the biological sample in the vial and transmitting the vial (e.g., to a clinic and/or a laboratory) to analyze the biological sample.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to explain the principles of the invention and its practical applications, they thereby enable others skilled in the art to utilize the invention and various embodiments with various modifications as are suited to the particular use contemplated. It is intended that the following claims and their equivalents define the scope of the invention.

The invention claimed is:

1. A universal single-handed device for self-collection of a biological sample, the single-handed device comprising:
    a sheath comprising a distal end for insertion into a portion of a user's body, the distal end of the sheath having a slit that forms at least two flexible segments;
    a shaft at least partially within the sheath having a collection head at a distal end thereof for collecting the biological sample;
    an actuator coupled to a proximal portion of the shaft to separate the at least two flexible segments upon advancement of the collection head; and
    a slider comprising a shaft-coupling portion coupled to a distal portion of the shaft and an extension protruding from an end face of the shaft-coupling portion in a longitudinal direction, wherein the extension is disposed below the collection head and is configured to support the collection head by abutment in a direction that intersects the longitudinal direction after the advancement of the collection head.

2. The universal single-handed device of claim 1, wherein the actuator is at least one of a knob, a roller, or a button.

3. The universal single-handed device of claim 1, wherein the extension is disposed at a distal end of the shaft-coupling portion of the slider.

4. The universal single-handed device of claim 3, wherein the collection head is configured to laterally deflect from the extension of the slider upon the advancement of the collection head through the flexible segments.

5. The universal single-handed device of claim 1, further comprising a handle attached to a proximal end of the sheath.

6. The universal single-handed device of claim 5, wherein the actuator is disposed within the handle.

7. The universal single-handed device of claim 1, wherein the actuator includes a feedback mechanism to aid the user in collecting the biological sample.

8. The universal single-handed device of claim 7, wherein the feedback mechanism comprises at least one of an audible feedback, a visual feedback, or a haptic feedback.

9. The universal single-handed device of claim 1, wherein the collection head comprises at least one of a brush, a sponge, a protrusion, or a bristle.

10. The universal single-handed device of claim 1, wherein the collection head includes a marker configured to react with the biological sample, thereby producing a visual change in the collection head.

11. The universal single-handed device of claim 1, wherein the collection head comprises a reticulated polyurethane having a density between 20 ppi and 90 ppi.

12. The universal single-handed device of claim 1, wherein the extension is further configured to accomplish at least one of protecting or guiding the collection head.

13. A method for self-collecting a biological sample, the method comprising:
    inserting a device into a lumen of a user's body, wherein the device comprises a sheath having a distal end, a shaft at least partially within the sheath, a collection head positioned at a distal end of the shaft, an actuator coupled to a proximal portion of the shaft; and a slider comprising a shaft-coupling portion coupled to a distal portion of the shaft and an extension protruding from an end face of the shaft-coupling portion in a longitudinal direction, wherein the distal end of the sheath has a slit that forms at least two flexible segments;
    actuating the actuator to advance the collection head and separate the at least two flexible segments, thereby allowing the collection head to pass distally therethrough and having the extension disposed below the collection head and supporting the collection head by abutment in a direction that intersects the longitudinal direction;
    rotating the collection head to collect the biological sample;
    actuating the actuator to retract the collection head into the sheath thereby allowing the at least two flexible segments to come together and at least partially cover the collection head; and
    withdrawing the device.

14. The method of claim 13, wherein the lumen of the user's body is a vaginal canal, and wherein the at least two flexible segments appose a vaginal wall of the user when the collection head is advanced distally through the at least two flexible segments.

15. The method of claim 14, further comprising aligning, via the at least two flexible segments, the collection head with the user's cervix.

16. The method of claim 15, further comprising displacing, via the at least two flexible segments, tissues surrounding the user's cervix.

17. The method of claim 13, further comprising deflecting vaginal tissue away from the collection head using the extension.

18. The method of claim 13, further comprising at least one of protecting or guiding the collection head using the extension.

19. The method of claim 13, wherein the biological sample comprises cervical cells.

20. The method of claim 13, wherein the biological sample comprises vaginal cells.

* * * * *